(12) United States Patent
Hoekstra et al.

(10) Patent No.: US 7,358,056 B1
(45) Date of Patent: Apr. 15, 2008

(54) METHODS FOR MODULATING SIGNAL TRANSDUCTION MEDIATED BY TGF-β AND RELATED PROTEINS

(75) Inventors: Merl F. Hoekstra, Cardiff-by-the-sea, CA (US); Weilin Xie, San Diego, CA (US); Brion W. Murray, San Diego, CA (US); Frank M. Mercurio, Del Mar, CA (US)

(73) Assignee: Signal Pharmaceuticals, San Diego, CA (US)

( * ) Notice: Subject to any disclaimer, the term of this patent is extended or adjusted under 35 U.S.C. 154(b) by 0 days.

(21) Appl. No.: 09/385,918

(22) Filed: Aug. 30, 1999

(51) Int. Cl.
*G01N 33/53* (2006.01)
(52) U.S. Cl. .................. 435/7.2; 435/7.1; 530/350
(58) Field of Classification Search ............... 435/7.2; 436/501; 530/350, 324
See application file for complete search history.

(56) References Cited

U.S. PATENT DOCUMENTS

| 6,001,619 | A | | 12/1999 | Beach et al. | 435/193 |
| 6,011,137 | A | * | 1/2000 | Pirozzi et al. | 530/324 |
| 6,060,262 | A | | 5/2000 | Beer-Romero et al. | 435/15 |
| 6,087,122 | A | * | 7/2000 | Husted et al. | 435/29 |
| 6,103,869 | A | | 8/2000 | Souchelnytokyi et al. | 530/330 |

FOREIGN PATENT DOCUMENTS

| WO | WO 99/01765 | 1/1999 |
| WO | WO 00/77168 | 12/2000 |

OTHER PUBLICATIONS

Zhu et al., A SMAD ubiquitin ligase targets the BMP pathway and affects embryonic differentiation. 1999, Nature vol. 400, pp. 687-693.*
Guo et al., PNAS, vol. 101, No. 25, pp. 9205-9210, 2004.*
Wells, Biochemistry, vol. 29, pp. 8509-8517, 1990.*
Attisano et al., 1993, "Identification of human activin and TGF beta type I receptors that form heteromeric kinase complexes with type II receptors", Cell 75(4):671-80.
Attisano et al., 1996, "Activation of signalling by the activin receptor complex", Mol Cell Biol. 16(3):1066-73.
Cui et al., 1996, "TGFbeta1 inhibits the formation of benign skin tumors, but enhances progression to invasive spindle carcinomas in transgenic mice", Cell 86(4):531-42.
Derynck, 1998, "Smads: transcriptional activators of TGF-beta responses", Cell 95(6):737-40. R.
Hayashi et al., 1997, "The MAD-related protein Smad7 associates with the TGFbeta receptor and functions as an antagonist of TGFbeta signaling", Cell 89(7):1165-73.
Heldin et al., 1997, "TGF-beta signalling from cell membrane to nucleus through SMAD proteins", Nature 390: 465-471.
Hershko et al., 1983, "Components of ubiquitin-protein ligase system. Resolution, affinity purification, and role in protein breakdown", J Biol Chem. 258(13):8206-14.

Hojo et al., 1999, "Cyclosporine induces cancer progression by a cell-autonomous mechanism", Nature 397(6719):530-4.
Huibregtse et al., 1995, A family of proteins structurally and functionally related to the E6-AP ubiquitin-protein ligase. Proc Natl Acad Sci U S A. 92(7):2563-7.
Huibregtse et al., 1993, "Cloning and expression of the cDNA for E6-AP, a protein that mediates the interaction of the human papillomavirus E6 oncoprotein with p53", Mol Cell Biol. 13(2):775-84.
Imamura, 1997, "Smad6 inhibits signalling by the TGF-beta superfamily", Nature 389(6651):622-6.
Kretzschmar et al., 1997, "Opposing BMP and EGF signalling pathways converge on the TGF-beta family mediator Smad1", Nature 389(6651):618-22.
Kretzschmar and Massague, 1998, "SMADs: mediators and regulators of TGF-beta signaling", Curr Opin Genet Dev. 8(1):103-11.
Lin et al., 1992, "Expression cloning of the TGF-beta type II receptor, a functional transmembrane serine/threonine kinase", Cell 68(4):775-85.
Liu et al., 1996, "A human Mad protein acting as a BMP-regulated transcriptional activator", Nature 381(6583):620-3.
Markowitz et al., 1995, "Inactivation of the type II TGF-beta receptor in colon cancer cells with microsatellite instability", Science 268(5215):1336-8.
Mathews and Vale, 1991, "Expression cloning of an activin receptor, a predicted transmembrane serine kinase", Cell. 65(6):973-82.
Miyazono et al., 1999, "Signal transduction by bone morphogenetic protein receptors", Bone 25(1): 91-93.
Nakao et al., 1997, "Identification of Smad2, a human Mad-related protein in the transforming growth factor beta signaling pathway", J Biol Chem. 272(5):2896-900.
Newfeld et al., 1996, "Mothers against dpp encodes a conserved cytoplasmic protein required in DPP/TGF-beta responsive cells", Development 122(7):2099-108.
Pirozzi et al., 1997, "Identification of novel human WW domain-containing proteins by cloning of ligand targets", J Biol Chem. 272(23):14611-6.
Reynisdottir et al., 1995, Kip/Cip and Ink4 Cdk inhibitors cooperate to induce cell cycle arrest in response to TGF-beta. Genes Dev. 9(15):1831-45.
Sekelsky et al., 1995, "Genetic characterization and cloning of mothers against dpp, a gene required for decapentaplegic function in *Drosophila* melanogaster", Genetics 139(3):1347-58.
Staub et al., 1996, "WW domains of Nedd4 bind to the proline-rich PY motifs in the epithelial Na+ channel deleted in Liddle's syndrome", EMBO J. 15(10):2371-80.
Sudol et al., 1996, "Structure and function of the WW domain", Prog Biophys Mol Biol. 5(1-2):113-32.

(Continued)

*Primary Examiner*—Hope Robinson
(74) *Attorney, Agent, or Firm*—Jones Day

(57) ABSTRACT

Methods are provided for identifying agents that modulate signaling mediated by transforming growth factor beta (TGF-β) and members of the TGF-β family, such as bone morphogenic protein (BMP). Such agents may be identified using screens that evaluate candidate agents for the ability to modulate Smad protein degradation. Agents identified as described herein may be used to augment or inhibit signaling mediated by one or more TGF-β family members in a variety of cell types and for therapeutic purposes.

18 Claims, 15 Drawing Sheets

OTHER PUBLICATIONS

Tsuchida et al., 1993, "Cloning and characterization of a transmembrane serine kinase that acts as an activin type I receptor", Proc Natl Acad Sci U S A. 90(23):11242-6.

Ulloa et al., 1999, Inhibition of transforming growth factor-beta/SMAD signalling by the interferon-gamma/STAT pathway. Nature 397(6721):710-3.

Zawel et al., 1998, "Human Smad3 and Smad4 are sequence-specific transcription activators", Mol Cell. 1(4):611-7.

Zhang et al., 1996, "Receptor-associated Mad homologues synergize as effectors of the TGF-beta response", Nature 383(6596):168-72.

Zhu et al., 1998, "Smad3 mutant mice develop metastatic colorectal cancer", Cell 94(6):703-14.

Zhu et al., 1999, "A SMAD ubiquitin ligase targets the BMP pathway and affects embryonic pattern formation", Nature 400: 687-93.

Wrana et al., 2000, "The Smad pathway," Cytokine & Growth Factor Reviews 11:5-13.

* cited by examiner

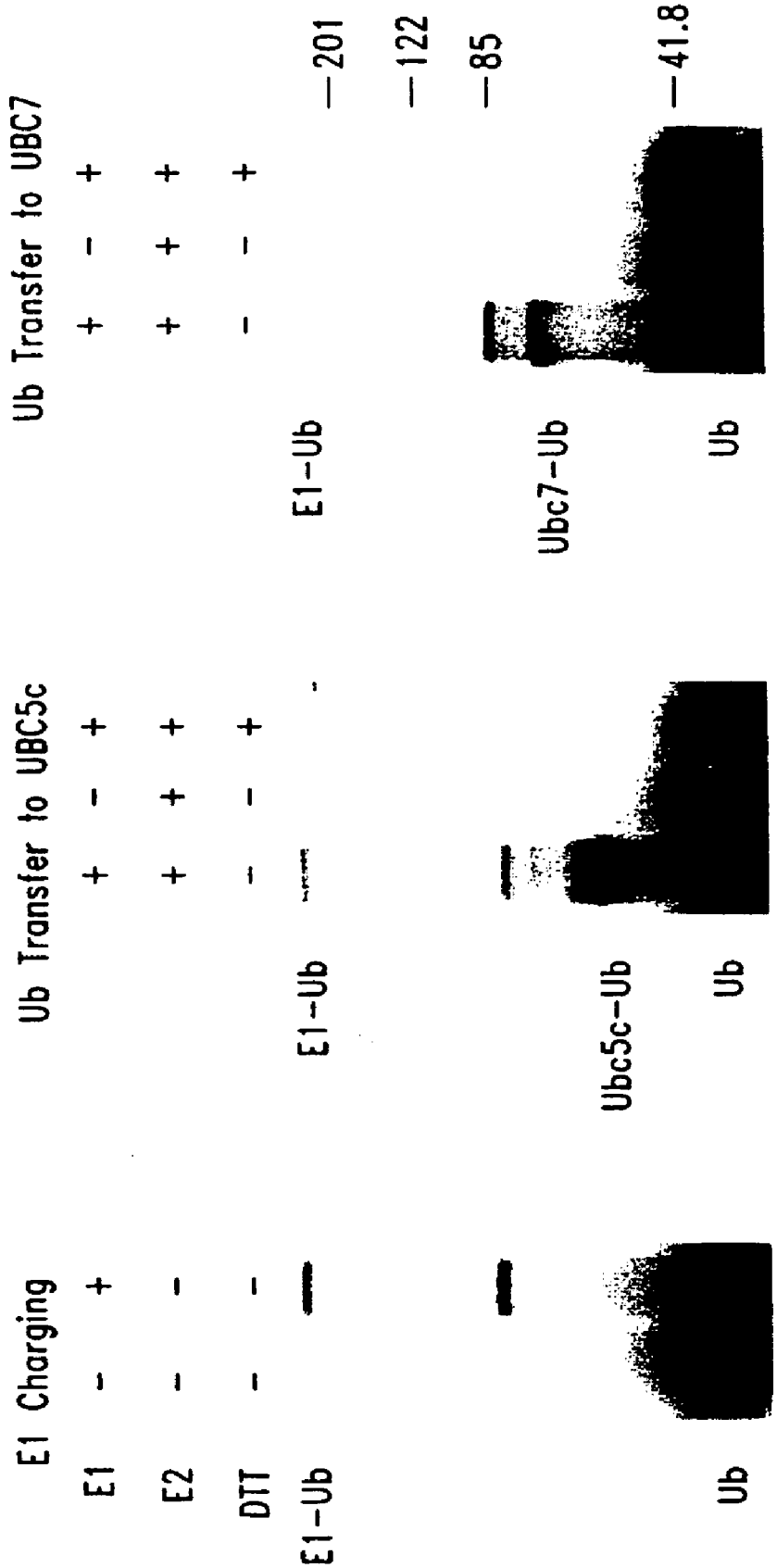

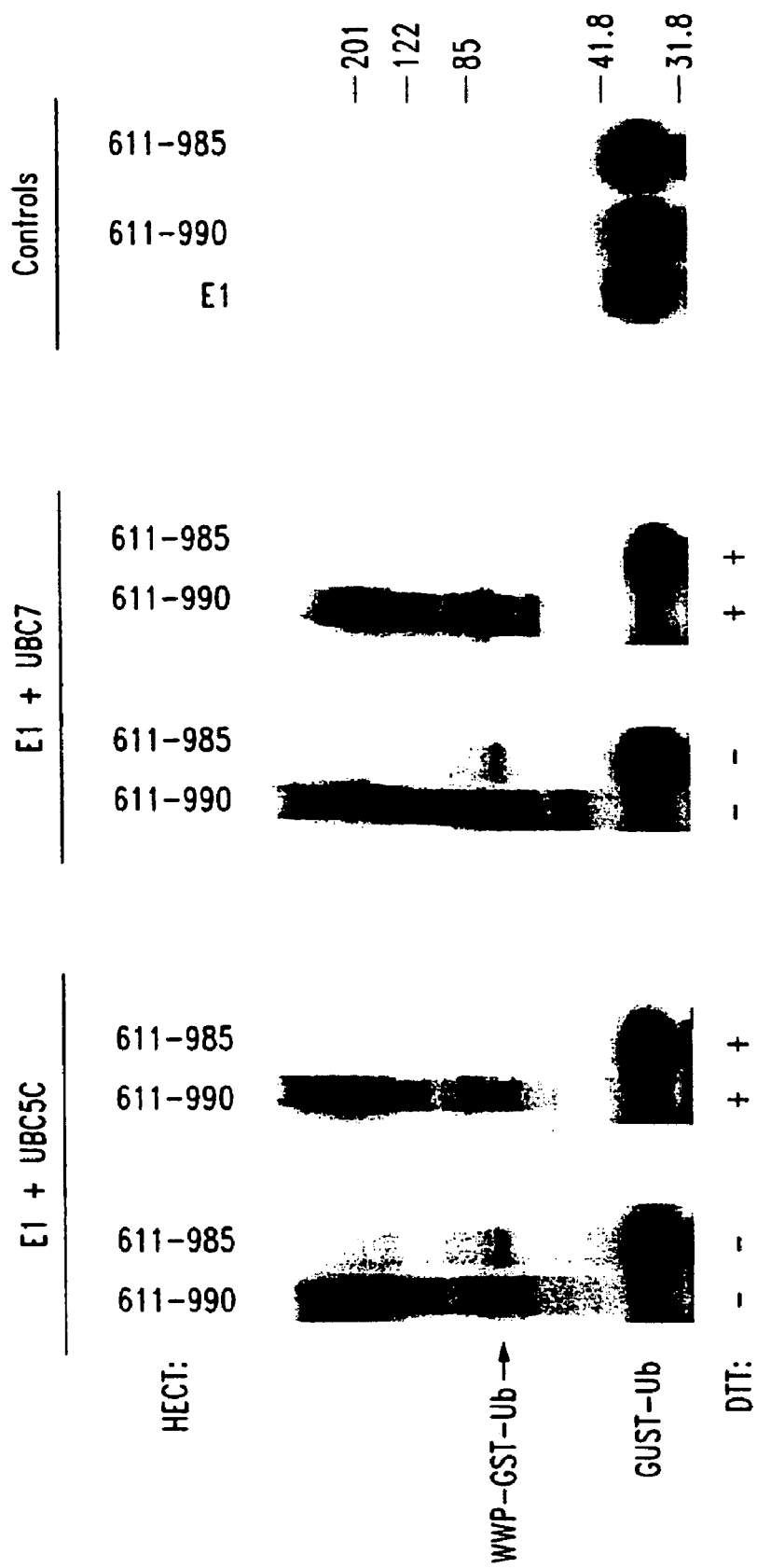

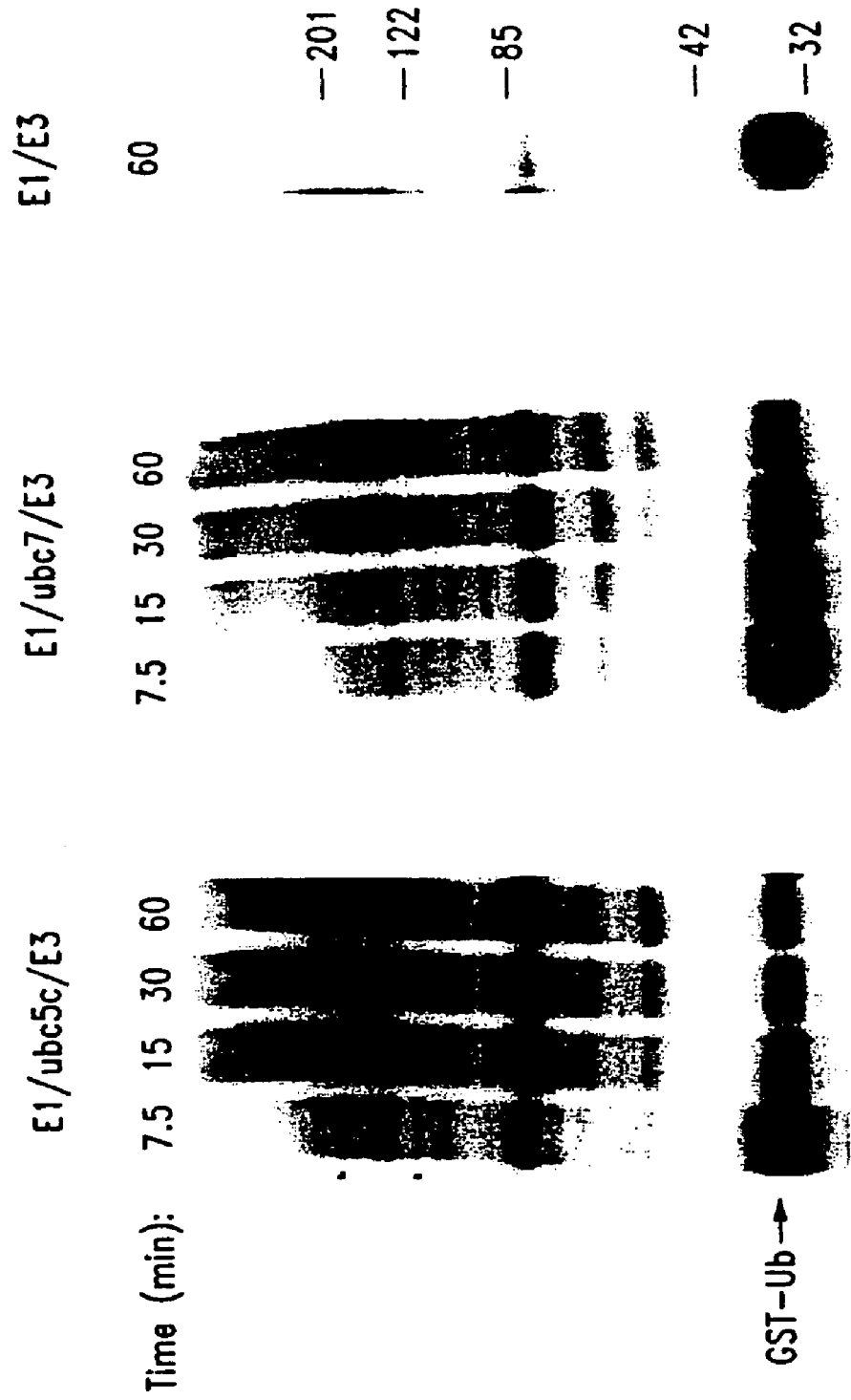

SEQUENCE LISTING

```
<160> NUMBER OF SEQ ID NOS: 32

<210> SEQ ID NO 1
<211> LENGTH: 108
<212> TYPE: PRT
<213> ORGANISM: Homo sapien
<220> FEATURE:
<221> NAME/KEY: VARIANT
<222> LOCATION: (1)...(1)
<223> OTHER INFORMATION: Xaa = Tyrosine or Phenylalanine
<220> FEATURE:
<221> NAME/KEY: VARIANT
<222> LOCATION: (2)...(4)
<223> OTHER INFORMATION: Xaa = any amino acid; 0-1 residues may be
      missing
<220> FEATURE:
<221> NAME/KEY: VARIANT
<222> LOCATION: (6)...(16)
<223> OTHER INFORMATION: Xaa = any amino acid; 0-3 residues may be
      missing
<220> FEATURE:
<221> NAME/KEY: VARIANT
<222> LOCATION: (20)...(20)
<223> OTHER INFORMATION: Xaa = any amino acid
<220> FEATURE:
<221> NAME/KEY: VARIANT
<222> LOCATION: (22)...(22)
<223> OTHER INFORMATION: Xaa = Valine, Isoleucine or Leucine
<220> FEATURE:
<221> NAME/KEY: VARIANT
<222> LOCATION: (23)...(27)
<223> OTHER INFORMATION: Xaa = any amino acid
<220> FEATURE:
<221> NAME/KEY: VARIANT
<222> LOCATION: (29)...(29)
<223> OTHER INFORMATION: Xaa = any amino acid
<220> FEATURE:
<221> NAME/KEY: VARIANT
<222> LOCATION: (30)...(30)
<223> OTHER INFORMATION: Xaa = Lysine or Arginine
<220> FEATURE:
<221> NAME/KEY: VARIANT
<222> LOCATION: (31)...(33)
<223> OTHER INFORMATION: Xaa = any amino acid
```

```
<220> FEATURE:
<221> NAME/KEY: VARIANT
<222> LOCATION: (34)...(34)
<223> OTHER INFORMATION: Xaa = Leucine or Valine
<220> FEATURE:
<221> NAME/KEY: VARIANT
<222> LOCATION: (37)...(37)
<223> OTHER INFORMATION: Xaa = Valine or Leucine
<220> FEATURE:
<221> NAME/KEY: VARIANT
<222> LOCATION: (40)...(40)
<223> OTHER INFORMATION: Xaa = Threonine or Serine
<220> FEATURE:
<221> NAME/KEY: VARIANT
<222> LOCATION: (41)...(41)
<223> OTHER INFORMATION: Xaa = any amino acid
<220> FEATURE:
<221> NAME/KEY: VARIANT
<222> LOCATION: (45)...(45)
<223> OTHER INFORMATION: Xaa = Leucine, Valine, Methionine, Alanine or
      Isoleucine
<220> FEATURE:
<221> NAME/KEY: VARIANT
<222> LOCATION: (46)...(46)
<223> OTHER INFORMATION: Xaa = any amino acid
<220> FEATURE:
<221> NAME/KEY: VARIANT
<222> LOCATION: (49)...(50)
<223> OTHER INFORMATION: Xaa = any amino acid
<220> FEATURE:
<221> NAME/KEY: VARIANT
<222> LOCATION: (52)...(61)
<223> OTHER INFORMATION: Xaa = any amino acid; 0-6 residues may be
      missing
<220> FEATURE:
<221> NAME/KEY: VARIANT
<222> LOCATION: (63)...(71)
<223> OTHER INFORMATION: Xaa = any amino acid; 0-2 residues may be
      missing
<220> FEATURE:
<221> NAME/KEY: VARIANT
<222> LOCATION: (74)...(75)
<223> OTHER INFORMATION: Xaa = any amino acid
<220> FEATURE:
<221> NAME/KEY: VARIANT
<222> LOCATION: (81)...(81)
<223> OTHER INFORMATION: Xaa = any amino acid
<220> FEATURE:
<221> NAME/KEY: VARIANT
<222> LOCATION: (86)...(86)
<223> OTHER INFORMATION: Xaa = any amino acid
<220> FEATURE:
<221> NAME/KEY: VARIANT
<222> LOCATION: (88)...(88)
<223> OTHER INFORMATION: Xaa = any amino acid
<220> FEATURE:
<221> NAME/KEY: VARIANT
<222> LOCATION: (90)...(92)
<223> OTHER INFORMATION: Xaa = any amino acid
<220> FEATURE:
<221> NAME/KEY: VARIANT
<222> LOCATION: (93)...(93)
<223> OTHER INFORMATION: Xaa = Leucine or Methionine
<220> FEATURE:
<221> NAME/KEY: VARIANT
<222> LOCATION: (94)...(95)
<223> OTHER INFORMATION: Xaa = any amino acid
<220> FEATURE:
<221> NAME/KEY: VARIANT
<222> LOCATION: (96)...(96)
<223> OTHER INFORMATION: Xaa = Arginine or Lysine
<220> FEATURE:
<221> NAME/KEY: VARIANT
<222> LOCATION: (98)...(99)
<223> OTHER INFORMATION: Xaa = any amino acid
<220> FEATURE:
<221> NAME/KEY: VARIANT
<222> LOCATION: (102)...(107)
<223> OTHER INFORMATION: Xaa = any amino acid; 0-2 residues may be
``` missing

<400> SEQUENCE: 1

Xaa Xaa Xaa Xaa Tyr Xaa Xaa Xaa Xaa Xaa Xaa Xaa Xaa Xaa Xaa
 1               5                   10                  15

Trp Phe Trp Xaa Ile Xaa Xaa Xaa Xaa Xaa Glu Xaa Xaa Xaa Xaa
            20                  25                  30

Xaa Xaa Gln Phe Xaa Thr Gly Xaa Xaa Arg Leu Pro Xaa Xaa Gly Phe
         35                  40                  45

Xaa Xaa Leu Xaa Xaa Xaa Xaa Xaa Xaa Xaa Xaa Xaa Ile Xaa Xaa
         50                  55                  60

Xaa Xaa Xaa Xaa Xaa Xaa Xaa Leu Pro Xaa Xaa His Thr Cys Phe Asn
65                  70                  75                  80

Xaa Leu Asp Leu Pro Xaa Tyr Xaa Ser Xaa Xaa Xaa Xaa Xaa Xaa Xaa
                 85                  90                  95

Leu Xaa Xaa Ala Ile Xaa Xaa Xaa Xaa Xaa Xaa Phe
         100                 105

<210> SEQ ID NO 2
<211> LENGTH: 33
<212> TYPE: PRT
<213> ORGANISM: Homo sapien
<220> FEATURE:
<221> NAME/KEY: VARIANT
<222> LOCATION: (5)...(5)
<223> OTHER INFORMATION: Xaa = any amino acid
<220> FEATURE:
<221> NAME/KEY: VARIANT
<222> LOCATION: (9)...(11)
<223> OTHER INFORMATION: Xaa = any amino acid
<220> FEATURE:
<221> NAME/KEY: VARIANT
<222> LOCATION: (12)...(14)
<223> OTHER INFORMATION: Xaa = independently selected polar amino acid
      (e.g., S,H,P,D,E,T or Y)
<220> FEATURE:
<221> NAME/KEY: VARIANT
<222> LOCATION: (16)...(16)
<223> OTHER INFORMATION: Xaa = independently selected polar amino acid
      (e.g., S,H,P,D,E,T or Y)
<220> FEATURE:
<221> NAME/KEY: VARIANT
<222> LOCATION: (17)...(17)
<223> OTHER INFORMATION: Xaa = any amino acid
<220> FEATURE:
<221> NAME/KEY: VARIANT
<222> LOCATION: (20)...(20)
<223> OTHER INFORMATION: Xaa = hydrophobic residue (e.g., I,V,L or M)
<220> FEATURE:
<221> NAME/KEY: VARIANT
<222> LOCATION: (21)...(21)
<223> OTHER INFORMATION: Xaa = any amino acid
<220> FEATURE:
<221> NAME/KEY: VARIANT
<222> LOCATION: (25)...(25)
<223> OTHER INFORMATION: Xaa = independently selected polar amino acid
      (e.g., S,H,P,D,E,T or Y)
<220> FEATURE:
<221> NAME/KEY: VARIANT
<222> LOCATION: (28)...(28)
<223> OTHER INFORMATION: Xaa = independently selected polar amino acid
      (e.g., S,H,P,D,E,T or Y)
<220> FEATURE:
<221> NAME/KEY: VARIANT
<222> LOCATION: (30)...(30)
<223> OTHER INFORMATION: Xaa = any amino acid
<220> FEATURE:
<221> NAME/KEY: VARIANT
<222> LOCATION: (31)...(31)
<223> OTHER INFORMATION: Xaa = independently selected polar amino acid
      (e.g., S,H,P,D,E,T or Y)

-continued

```
<220> FEATURE:
<221> NAME/KEY: VARIANT
<222> LOCATION: (33)...(33)
<223> OTHER INFORMATION: Xaa = independently selected polar amino acid
      (e.g., S,H,P,D,E,T or Y)

<400> SEQUENCE: 2

Gly Pro Leu Pro Xaa Gly Trp Glu Xaa Xaa Xaa Xaa Xaa Gly Xaa
1               5                   10                  15

Xaa Tyr Tyr Xaa Xaa His Asn Thr Xaa Thr Thr Xaa Trp Xaa Xaa Pro
            20                  25                  30

Xaa

<210> SEQ ID NO 3
<211> LENGTH: 38
<212> TYPE: PRT
<213> ORGANISM: Homo sapien

<400> SEQUENCE: 3

Ser Pro Leu Pro Pro Gly Trp Glu Glu Arg Gln Asp Ile Leu Gly Arg
1               5                   10                  15

Thr Tyr Tyr Val Asn His Glu Ser Arg Arg Thr Gln Trp Lys Arg Pro
            20                  25                  30

Thr Pro Gln Asp Asn Leu
            35

<210> SEQ ID NO 4
<211> LENGTH: 38
<212> TYPE: PRT
<213> ORGANISM: Homo sapien

<400> SEQUENCE: 4

Ser Gly Leu Pro Pro Gly Trp Glu Glu Arg Gln Asp Ile Leu Gly Arg
1               5                   10                  15

Thr Tyr Tyr Val Asn His Glu Ser Arg Arg Thr Gln Trp Lys Arg Pro
            20                  25                  30

Thr Pro Gln Asp Asn Leu
            35

<210> SEQ ID NO 5
<211> LENGTH: 38
<212> TYPE: PRT
<213> ORGANISM: Homo sapien

<400> SEQUENCE: 5

Gly Phe Leu Pro Lys Gly Trp Glu Val Arg His Ala Pro Asn Gly Arg
1               5                   10                  15

Pro Phe Phe Ile Asp His Asn Thr Lys Thr Thr Thr Trp Glu Asp Pro
            20                  25                  30

Arg Leu Lys Ile Pro Ala
            35

<210> SEQ ID NO 6
<211> LENGTH: 38
<212> TYPE: PRT
<213> ORGANISM: Homo sapien

<400> SEQUENCE: 6

Gly Pro Leu Pro Pro Gly Trp Glu Glu Arg Thr His Thr Asp Gly Arg
1               5                   10                  15

Ile Phe Tyr Ile Asn His Asn Ile Lys Arg Thr Gln Trp Glu Asp Pro
```

```
                    20                  25                  30

Arg Leu Glu Asn Val Ala
            35

<210> SEQ ID NO 7
<211> LENGTH: 38
<212> TYPE: PRT
<213> ORGANISM: Saccharomyces cerevisiae

<400> SEQUENCE: 7

Gly Arg Leu Pro Pro Gly Trp Glu Arg Arg Thr Asp Asn Phe Gly Arg
  1               5                  10                  15

Thr Tyr Tyr Val Asp His Asn Thr Arg Thr Thr Thr Trp Lys Arg Pro
                 20                  25                  30

Thr Leu Asp Gln Thr Glu
            35

<210> SEQ ID NO 8
<211> LENGTH: 38
<212> TYPE: PRT
<213> ORGANISM: Saccharomyces cerevisiae

<400> SEQUENCE: 8

Gly Glu Leu Pro Ser Gly Trp Glu Gln Arg Phe Thr Pro Glu Gly Arg
  1               5                  10                  15

Ala Tyr Phe Val Asp His Asn Thr Arg Thr Thr Thr Trp Val Asp Pro
                 20                  25                  30

Arg Arg Gln Gln Tyr Ile
            35

<210> SEQ ID NO 9
<211> LENGTH: 38
<212> TYPE: PRT
<213> ORGANISM: Saccharomyces cerevisiae

<400> SEQUENCE: 9

Gly Pro Leu Pro Ser Gly Trp Glu Met Arg Leu Thr Asn Thr Ala Arg
  1               5                  10                  15

Val Tyr Phe Val Asp His Asn Thr Lys Thr Thr Thr Trp Asp Asp Pro
                 20                  25                  30

Arg Leu Pro Ser Ser Leu
            35

<210> SEQ ID NO 10
<211> LENGTH: 38
<212> TYPE: PRT
<213> ORGANISM: Homo sapien

<400> SEQUENCE: 10

Leu Pro Ser Gly Trp Gly Trp Glu Gln Arg Lys Asp Pro His Gly Arg
  1               5                  10                  15

Thr Tyr Tyr Val Asp His Asn Thr Arg Thr Thr Thr Trp Glu Arg Pro
                 20                  25                  30

Gln Pro Leu Pro Pro Gly
            35

<210> SEQ ID NO 11
<211> LENGTH: 38
<212> TYPE: PRT
<213> ORGANISM: Homo sapien
```

-continued

```
<400> SEQUENCE: 11

Gln Pro Leu Pro Pro Gly Trp Glu Arg Arg Val Asp Asp Arg Arg
1               5                   10                  15

Val Tyr Tyr Val Asp His Asn Thr Arg Thr Thr Thr Trp Gln Arg Pro
                20                  25                  30

Thr Met Glu Ser Val Arg
            35

<210> SEQ ID NO 12
<211> LENGTH: 38
<212> TYPE: PRT
<213> ORGANISM: Homo sapien

<400> SEQUENCE: 12

Gly Pro Leu Pro Pro Gly Trp Glu Lys Arg Val Asp Ser Thr Asp Arg
1               5                   10                  15

Val Tyr Phe Val Asn His Asn Thr Lys Thr Thr Gln Trp Glu Asp Pro
                20                  25                  30

Arg Thr Gln Gly Leu Gln
            35

<210> SEQ ID NO 13
<211> LENGTH: 38
<212> TYPE: PRT
<213> ORGANISM: Homo sapien

<400> SEQUENCE: 13

Glu Pro Leu Pro Glu Gly Trp Glu Ile Arg Tyr Thr Arg Glu Gly Val
1               5                   10                  15

Arg Tyr Phe Val Asp His Asn Thr Arg Thr Thr Thr Phe Lys Asp Pro
                20                  25                  30

Arg Asn Gly Lys Ser Ser
            35

<210> SEQ ID NO 14
<211> LENGTH: 4
<212> TYPE: PRT
<213> ORGANISM: Homo sapien
<220> FEATURE:
<221> NAME/KEY: VARIANT
<222> LOCATION: (3)...(3)
<223> OTHER INFORMATION: Xaa = any amino acid

<400> SEQUENCE: 14

Pro Pro Xaa Tyr
1

<210> SEQ ID NO 15
<211> LENGTH: 6
<212> TYPE: PRT
<213> ORGANISM: Homo sapien
<220> FEATURE:
<221> NAME/KEY: VARIANT
<222> LOCATION: (1)...(1)
<223> OTHER INFORMATION: Xaa = Serine or Threonine
<220> FEATURE:
<221> NAME/KEY: VARIANT
<222> LOCATION: (5)...(5)
<223> OTHER INFORMATION: Xaa = Proline, Alanine or Glycine

<400> SEQUENCE: 15

Xaa Pro Pro Pro Xaa Tyr
1               5
```

-continued

```
<210> SEQ ID NO 16
<211> LENGTH: 6
<212> TYPE: PRT
<213> ORGANISM: Homo sapien

<400> SEQUENCE: 16

Thr Pro Pro Pro Ala Tyr
 1               5

<210> SEQ ID NO 17
<211> LENGTH: 14
<212> TYPE: PRT
<213> ORGANISM: Homo sapien
<220> FEATURE:
<221> NAME/KEY: VARIANT
<222> LOCATION: (10)...(10)
<223> OTHER INFORMATION: Xaa = Leucine or Methionine

<400> SEQUENCE: 17

Pro Ala Asp Thr Pro Pro Pro Ala Tyr Xaa Pro Pro Pro Asp
 1               5                  10

<210> SEQ ID NO 18
<211> LENGTH: 6
<212> TYPE: PRT
<213> ORGANISM: Homo sapien

<400> SEQUENCE: 18

Thr Pro Pro Pro Gly Tyr
 1               5

<210> SEQ ID NO 19
<211> LENGTH: 11
<212> TYPE: PRT
<213> ORGANISM: Homo sapien
<220> FEATURE:
<221> NAME/KEY: VARIANT
<222> LOCATION: (7)...(7)
<223> OTHER INFORMATION: Xaa = Isoleucine or Leucine

<400> SEQUENCE: 19

Thr Pro Pro Pro Gly Tyr Xaa Ser Glu Asp Gly
 1               5                  10

<210> SEQ ID NO 20
<211> LENGTH: 14
<212> TYPE: PRT
<213> ORGANISM: Homo sapien

<400> SEQUENCE: 20

Glu Leu Glu Ser Pro Pro Pro Tyr Ser Arg Tyr Pro Met
 1               5                  10

<210> SEQ ID NO 21
<211> LENGTH: 14
<212> TYPE: PRT
<213> ORGANISM: Homo sapien

<400> SEQUENCE: 21

Gly Pro Glu Ser Pro Pro Pro Tyr Ser Arg Leu Ser Pro
 1               5                  10

<210> SEQ ID NO 22
<211> LENGTH: 14
<212> TYPE: PRT
<213> ORGANISM: Homo sapien
```

```
<400> SEQUENCE: 22

Pro Ala Asp Thr Pro Pro Pro Ala Tyr Leu Pro Pro Glu Asp
1               5                   10

<210> SEQ ID NO 23
<211> LENGTH: 14
<212> TYPE: PRT
<213> ORGANISM: Homo sapien

<400> SEQUENCE: 23

Pro Ala Asp Thr Pro Pro Pro Ala Tyr Met Pro Pro Asp Asp
1               5                   10

<210> SEQ ID NO 24
<211> LENGTH: 14
<212> TYPE: PRT
<213> ORGANISM: Homo sapien

<400> SEQUENCE: 24

Ile Pro Glu Thr Pro Pro Pro Gly Tyr Ile Ser Glu Asp Gly
1               5                   10

<210> SEQ ID NO 25
<211> LENGTH: 14
<212> TYPE: PRT
<213> ORGANISM: Homo sapien

<400> SEQUENCE: 25

Ala Gly Leu Thr Pro Pro Pro Gly Tyr Leu Ser Glu Asp Gly
1               5                   10

<210> SEQ ID NO 26
<211> LENGTH: 38
<212> TYPE: PRT
<213> ORGANISM: Homo sapien

<400> SEQUENCE: 26

Leu Pro Ser Gly Trp Glu Gln Arg Lys Asp Pro His Gly Arg Thr Tyr
1               5                   10                  15

Tyr Val Asp His Asn Thr Arg Thr Thr Thr Trp Glu Arg Pro Gln Pro
                20                  25                  30

Leu Pro Pro Gly Trp Glu
            35

<210> SEQ ID NO 27
<211> LENGTH: 14
<212> TYPE: PRT
<213> ORGANISM: Homo sapien

<400> SEQUENCE: 27

Pro Ala Asp Thr Pro Pro Pro Ala His Leu Pro Pro Glu Asp
1               5                   10

<210> SEQ ID NO 28
<211> LENGTH: 14
<212> TYPE: PRT
<213> ORGANISM: Homo sapien

<400> SEQUENCE: 28

His Pro Gly Thr Pro Pro Pro Tyr Thr Val Gly Pro Gly
1               5                   10
```

-continued

```
<210> SEQ ID NO 29
<211> LENGTH: 14
<212> TYPE: PRT
<213> ORGANISM: Homo sapien

<400> SEQUENCE: 29

Ile Pro Gly Thr Pro Pro Asn Tyr Asp Ser Leu Arg Leu
1               5                   10

<210> SEQ ID NO 30
<211> LENGTH: 14
<212> TYPE: PRT
<213> ORGANISM: Homo sapien

<400> SEQUENCE: 30

Ile Pro Gly Thr Pro Pro Asn His Asp Ser Leu Arg Leu
1               5                   10

<210> SEQ ID NO 31
<211> LENGTH: 375
<212> TYPE: PRT
<213> ORGANISM: Homo sapien

<400> SEQUENCE: 31

Gly Phe Arg Trp Lys Leu Ala His Phe Arg Tyr Leu Cys Gln Ser Asn
1               5                   10                  15

Ala Leu Pro Ser His Val Lys Ile Asn Val Ser Arg Gln Thr Leu Phe
            20                  25                  30

Glu Asp Ser Phe Gln Gln Ile Met Ala Leu Lys Pro Tyr Asp Leu Arg
        35                  40                  45

Arg Arg Leu Tyr Val Ile Phe Arg Gly Glu Glu Gly Leu Asp Tyr Gly
    50                  55                  60

Gly Leu Ala Arg Glu Trp Phe Phe Leu Leu Ser His Glu Val Leu Asn
65                  70                  75                  80

Pro Met Tyr Cys Leu Phe Glu Tyr Ala Gly Lys Asn Asn Tyr Cys Leu
                85                  90                  95

Gln Ile Asn Pro Ala Ser Thr Ile Asn Pro Asp His Leu Ser Tyr Phe
            100                 105                 110

Cys Phe Ile Gly Arg Phe Ile Ala Met Ala Leu Phe His Gly Lys Phe
        115                 120                 125

Ile Asp Thr Gly Phe Ser Leu Pro Phe Tyr Lys Arg Met Leu Ser Lys
    130                 135                 140

Lys Leu Thr Ile Lys Asp Leu Glu Ser Ile Asp Thr Glu Phe Tyr Asn
145                 150                 155                 160

Ser Leu Ile Trp Ile Arg Asp Asn Asn Ile Glu Glu Cys Gly Leu Glu
                165                 170                 175

Met Tyr Phe Ser Val Asp Met Glu Ile Leu Gly Lys Val Thr Ser His
            180                 185                 190

Asp Leu Lys Leu Gly Gly Ser Asn Ile Leu Val Thr Glu Glu Asn Lys
        195                 200                 205

Asp Glu Tyr Ile Gly Leu Met Thr Glu Trp Arg Phe Ser Arg Gly Val
    210                 215                 220

Gln Glu Gln Thr Lys Ala Phe Leu Asp Gly Phe Asn Glu Val Val Pro
225                 230                 235                 240

Leu Gln Trp Leu Gln Tyr Phe Asp Glu Lys Glu Leu Glu Val Met Leu
                245                 250                 255

Cys Gly Met Gln Glu Val Asp Leu Ala Asp Trp Gln Arg Asn Thr Val
            260                 265                 270
```

```
Tyr Arg His Tyr Thr Arg Asn Ser Lys Gln Ile Ile Trp Phe Trp Gln
            275                 280                 285

Phe Val Lys Glu Thr Asp Asn Glu Val Arg Met Arg Leu Leu Gln Phe
        290                 295                 300

Val Thr Gly Thr Cys Arg Leu Pro Leu Gly Gly Phe Ala Glu Leu Met
305                 310                 315                 320

Gly Ser Asn Gly Pro Arg Asn Ser Gln Lys Phe Cys Ile Glu Lys Val
                325                 330                 335

Gly Lys Asp Thr Trp Leu Pro Arg Ser His Thr Cys Phe Asn Arg Leu
            340                 345                 350

Asp Leu Pro Pro Tyr Lys Ser Tyr Glu Gln Leu Lys Glu Lys Leu Leu
            355                 360                 365

Phe Ala Ile Glu Glu Thr Glu
            370                 375

<210> SEQ ID NO 32
<211> LENGTH: 380
<212> TYPE: PRT
<213> ORGANISM: Homo sapien

<400> SEQUENCE: 32

Gly Phe Arg Trp Lys Leu Ala His Phe Arg Tyr Leu Cys Gln Ser Asn
1               5                   10                  15

Ala Leu Pro Ser His Val Lys Ile Asn Val Ser Arg Gln Thr Leu Phe
            20                  25                  30

Glu Asp Ser Phe Gln Gln Ile Met Ala Leu Lys Pro Tyr Asp Leu Arg
        35                  40                  45

Arg Arg Leu Tyr Val Ile Phe Arg Gly Glu Gly Leu Asp Tyr Gly
    50                  55                  60

Gly Leu Ala Arg Glu Trp Phe Phe Leu Leu Ser His Glu Val Leu Asn
65                  70                  75                  80

Pro Met Tyr Cys Leu Phe Glu Tyr Ala Gly Lys Asn Asn Tyr Cys Leu
                85                  90                  95

Gln Ile Asn Pro Ala Ser Thr Ile Asn Pro Asp His Leu Ser Tyr Phe
            100                 105                 110

Cys Phe Ile Gly Arg Phe Ile Ala Met Ala Leu Phe His Gly Lys Phe
        115                 120                 125

Ile Asp Thr Gly Phe Ser Leu Pro Phe Tyr Lys Arg Met Leu Ser Lys
    130                 135                 140

Lys Leu Thr Ile Lys Asp Leu Glu Ser Ile Asp Thr Glu Phe Tyr Asn
145                 150                 155                 160

Ser Leu Ile Trp Ile Arg Asp Asn Asn Ile Glu Glu Cys Gly Leu Glu
                165                 170                 175

Met Tyr Phe Ser Val Asp Met Glu Ile Leu Gly Lys Val Thr Ser His
            180                 185                 190

Asp Leu Lys Leu Gly Gly Ser Asn Ile Leu Val Thr Glu Glu Asn Lys
        195                 200                 205

Asp Glu Tyr Ile Gly Leu Met Thr Glu Trp Arg Phe Ser Arg Gly Val
    210                 215                 220

Gln Glu Gln Thr Lys Ala Phe Leu Asp Gly Phe Asn Glu Val Val Pro
225                 230                 235                 240

Leu Gln Trp Leu Gln Tyr Phe Asp Glu Lys Glu Leu Glu Val Met Leu
                245                 250                 255

Cys Gly Met Gln Glu Val Asp Leu Ala Asp Trp Gln Arg Asn Thr Val
```

```
                          260                 265                 270
Tyr Arg His Tyr Thr Arg Asn Ser Lys Gln Ile Ile Trp Phe Trp Gln
        275                 280                 285

Phe Val Lys Glu Thr Asp Asn Glu Val Arg Met Arg Leu Leu Gln Phe
        290                 295                 300

Val Thr Gly Thr Cys Arg Leu Pro Leu Gly Gly Phe Ala Glu Leu Met
305                 310                 315                 320

Gly Ser Asn Gly Pro Arg Asn Ser Gln Lys Phe Cys Ile Glu Lys Val
                325                 330                 335

Gly Lys Asp Thr Trp Leu Pro Arg Ser His Thr Cys Phe Asn Arg Leu
                340                 345                 350

Asp Leu Pro Pro Tyr Lys Ser Tyr Glu Gln Leu Lys Glu Lys Leu Leu
        355                 360                 365

Phe Ala Ile Glu Glu Thr Glu Gly Phe Gly Gln Glu
        370                 375                 380
```

METHODS FOR MODULATING SIGNAL TRANSDUCTION MEDIATED BY TGF-β AND RELATED PROTEINS

TECHNICAL FIELD

The present invention relates generally to methods for identifying agents that modulate signaling mediated by transforming growth factor beta (TGF-β) and members of the TGF-β family, such as bone morphogenic protein (BMP). The invention is more particularly related to screens for use in evaluating agents for the ability to modulate Smad protein degradation, and to methods using such agents to augment or inhibit BMP-mediated signaling in a variety of cell types.

BACKGROUND OF THE INVENTION

The transforming growth factor beta (TGF-β) superfamily is a large family of multifunctional proteins that regulate a variety of cellular functions, including cellular proliferation, migration, differentiation and apoptosis. TGF-β,∴ the founding member of TGF-β family, has been shown to play a variety of roles ranging from embryonic pattern formation to cell growth regulation in adult tissues. TGF-β exerts its biological functions by signal transduction cascades that ultimately activate and/or suppress expression of a set of specific genes. Other TGF-beta family members include activins, inhibins and Bone Morphogenic Proteins (BMPs). BMP-mediated signal transduction is important for a variety of normal processes, including bone growth and the function of the nervous system, eyes and organs such as kidneys.

TGF-β family members generally initiate signal transduction by first binding to a receptor. TGF-β, for example, triggers its signal by first binding to its type II receptor, then recruiting and activating its type I receptors. The activated type I receptors then phosphorylate its intracellular signal transducer molecules, the Smad proteins (Heldin et al., *Nature* 390:465-471, 1997; Derynck et al., *Cell* 95:737-740, 1998). Similarly, BMP binds to a BMP serine/threonine transmembrane receptor protein kinases. The signals are further transduced from the receptors to the nuclei, resulting in altered patterns of gene expression. Signal transduction from BMP receptor to nuclei is known to involve Smad family proteins, certain of which become incorporated into transcriptional complexes and activate downstream genes.

Smads are receptor-activated, signal transducing transcription factors that transmit signals from TGF-β family receptors. Members of the Smad family of proteins have been identified based on homology to the *Drosophilia* gene Mothers against dpp (mad), which encodes an essential element in the *Drosophilia* dpp signal transduction pathway (see Sekelsky et al., *Genetics* 139:1347-1358, 1995; Newfeld et al., *Development* 122:2099-2108, 1996). Smad proteins are generally characterized by highly conserved amino- and carboxy-terminal domains separated by a proline-rich linker. The amino terminal domain (the MH1 domain) mediates DNA binding, and the carboxy terminal domain (the MH2 domain) associates with the receptor.

To date, eight Smad proteins have been identified and shown to participate in signal responses induced by TGF-β family members (see Kretzschmar and Massague, *Current Opinion in Genetics and Development* 8:103-111, 1998). These Smads can be divided into three subgroups. One group (Smads1, 2, 3, 5 and 8) induces Smads that are direct substrates of a TGF-β family receptor kinase. Another group (Smad 4) includes Smads that are not direct receptor substrates, but participate in signaling by associating with receptor-activated Smads. The third group of Smads (Smad6 and Smad7) consists of proteins that inhibit activation of Smads in the first two groups.

Smads have specific roles in pathways of different TGF-β family members. Among Smad proteins identified for TGF-β family members, Smad2 and Smad3 are specific for TGF-β signaling (Heldin et al., *Nature* 390:465-475, 1997). The activated Smad2 and Smad3 interact with common mediator Smad4 and translocate into nuclei, where they activate a set of specific genes (Heldin et al., *Nature*, 390:465-471, 1997). The TGF-β pathway uses the signal inhibitory proteins Smad6 and Smad7 to balance the net output of the signaling, as well as direct activation of Smad2 and/or Smad3. In the case of BMP-mediated signaling, following binding of a BMP to a BMP receptor, Smad1 and Smad5 are recruited to the receptor and phosphorylated. Once these proteins are phosphorylated, Smad1 and Smad5 form a complex with Smad4, and the complex translocates to the nucleus, resulting in activation of BMP-mediated gene transcription.

While Smad2 and Smad3 have intrinsic transactivation activity as transcription factors (Zawel et al., *Mol Cell* 1:611-617, 1998), studies have demonstrated that they activate specific gene expression largely through specifically interacting with other nuclear factors (Derynck et al., *Cell* 95:737-740, 1998). A specific TGF-β-mediated effect on a given cell type can be achieved by activating a specific Smad protein, resulting in alterations in expression of specific genes. The interplay or crosstalk of different signal transduction pathways is essential to provide balanced and integrated response to total signals to a given cell under given conditions. TGF-β-induced signaling has been found to crosstalk at the Smad level with Ras-mediated MAP kinase pathway and Jak/Stat pathway (Ulloa et al., *Nature* 397:710-3, 1999, Kretzschmar et al., *Nature* 389:618-22, 1997).

As noted above, TGF-β plays a role in the regulation of cell growth. TGF-β can be a growth stimulator or growth inhibitor, depending on the type or/and growth stage of the responding cells. As a potent negative epithelial cell growth regulator, TGF-β plays an important role in epithelial carcinogenesis (Cui et al., *Cell*, 86:531-542, 1996). TGF-β has been shown to cause cell growth arrest by inducing cyclin-dependent kinase inhibitors such as p15 and p21 (Hannon et al., *Genes Dev.* 9:1831-45, 1995), and a TGF-β type II receptor mutation that makes cells resistant to TGF-β leads to an enhancement of tumorigenic state of cells (Markowitz et al., *Science* 268:1336-8, 1995). Mutations in Smad genes have also been associated with cancer. Some colon cancers have found to carry mutations in tumor suppressor protein Smad2 (Eppert et al., *Cell* 88:543-552, 1996; Hata et al., *Nature* 388:82-87, 1997). It also has been shown that Smad4 is a tumor suppressor gene in human pancreatic carcinomas and perhaps in other tumors. Smad3 mutant mice develop metastatic colorectal cancer (Zhu et al., *Cell* 94:703-714, 1998), suggesting that Smad3 may play role in human colon cancer. In other contexts, TGF-β and TGF-β pathway members appear to play cell growth promoting roles. At early stages of carcinogenesis, TGF-β has been reported to act as a tumor promoter. At later stage, TGF-β can stimulate malignant progression. It has recently been demonstrated that TGF-β is directly involved in promoting malignancy following organ transplantation (Hojo et al., *Nature* 397:530-534, 1999). Thus, TGF-β can promote tumor cell invasion and metastasis, and methods for modulating TGF-β signaling could provide opportunities to develop effective cancer therapy.

Although certain aspects of TGF-β- and BMP-mediated signaling are understood, further knowledge of these signaling pathways is needed to facilitate the development of therapeutic agents that modulate such signaling. Accordingly, there is a need in the art for an improved understanding of the molecular mechanisms of TGF-β- and BMP-mediated signaling and for the development of agents that modulate such signaling. The present invention fulfills these needs and further provides other related advantages.

SUMMARY OF THE INVENTION

Briefly stated, the present invention provides methods for identifying agents that modulate signal transduction mediated by TGF-β and/or other member(s) of the TGF-β family, such as BMP. Within certain aspects, such methods comprise the steps of (a) contacting (i) a first polypeptide comprising a HECT E3 ubiquitin ligase WW domain, or a variant thereof in which the ability of the polypeptide to bind to a Smad protein is not substantially diminished relative to the HECT E3 ubiquitin ligase; (ii) a second polypeptide comprising a Smad PY motif, or a variant thereof in which the ability of the polypeptide to bind to an E3 ubiquitin ligase is not substantially diminished relative to a native Smad protein comprising the PY motif; and (iii) a candidate agent; wherein the step of contacting is performed under conditions that permit a detectable level of binding of the first polypeptide to the second polypeptide in the absence of candidate agent; (b) determining a level of binding of the first polypeptide to the second polypeptide; and (c) comparing the level of binding to a control level of binding of the first polypeptide to the second polypeptide in the absence of candidate agent.

Within other aspects, such methods comprise the steps of: (a) contacting (i) a candidate agent; (ii) a ubiquitinated HECT E3 ubiquitin ligase; and (iii) a Smad protein or a variant thereof that comprises a PY motif; wherein the contact takes place under conditions and for a time sufficient to permit ubiquitination of the Smad protein or variant thereof by the HECT E3 ubiquitin ligase in the absence of candidate agent; (b) determining a level of ubiquitination of the Smad protein or variant thereof; and (c) comparing the level of ubiquitination to a control level of ubiquitination in the absence of candidate agent.

Within further aspects, such methods comprise the steps of: (a) contacting a cell that expresses a TGF-β or BMP receptor with BMP or TGF-β, and a candidate agent; and (b) detecting a level of a Smad protein in the bone cell, relative to a level of the Smad protein in a cell that is contacted with the bone morphogenic protein in the absence of the candidate agent.

Still further such methods comprise the steps of: (a) contacting a cell that expresses a TGF-β or BMP receptor with TGF-β or BMP and a candidate agent; and (b) detecting a level of ubiquitination of a Smad protein in the cell, relative to a level of the Smad protein ubiquitination in a cell that is contacted with the bone morphogenic protein but is not contacted with the candidate agent.

Within other such aspects, a method for screening for an agent that modulates TGF-β- or BMP-mediated signaling comprises the steps of: (a) contacting a cell that expresses a TGF-β or BMP receptor with TGF-β or BMP and a candidate agent; and (b) detecting a level of a HECT E3 ubiquitin ligase activity in the cell, relative to a level of HECT E3 ubiquitin ligase activity in a cell that is contacted with TGF-β or BMP in the absence of the candidate agent.

The present invention further provides, within other aspects, methods for augmenting TGF-β- or BMP-mediated signaling in a cell, comprising contacting a cell with an agent that inhibits binding of a HECT E3 ubiquitin ligase WW domain to a Smad PY motif and/or inhibits ubiquitination of a Smad protein.

Within further aspects, the present invention provides methods for stimulating bone formation in a patient, comprising administering to a patient a therapeutically effective amount of an agent that inhibits binding of a HECT E3 ubiquitin ligase WW domain to a Smad PY motif and/or inhibits ubiquitination of a Smad protein.

The present invention further provides, within other aspects, methods for preventing or treating a condition associated with insufficient TGF-β- or BMP-mediated cell signaling, comprising administering to a patient a therapeutically effective amount of an agent that inhibits binding of a HECT E3 ubiquitin ligase WW domain to a Smad PY motif and/or inhibits ubiquitination of a Smad protein.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

In FIG. 8A, binding to four GST fusion peptides (GST-WWP1.1, GST-WWP1.2, GST-WWP1.3 and GST-WWP1.4) is shown, as well as binding to RSP5.2 WW domain. WW domain peptides were coated on polystyrene plates at the indicated receptor coating concentrations, and blocked with BSA. Biotinylated PY motif peptide was then added at the indicated concentrations. Binding was assessed using a time-resolved fluorescence assay and is shown as cps. FIG. 8B presents a Scatchard analysis of the Smad7 PY motif to WWP1.2 and WWP1.4, as indicated.

FIGS. 9A-9C are autoradiograms illustrating the activation and activity of E1 in a coupled ubiquitination assay. FIG. 9A shows ubiquitinated E1 (lane 2), where the presence of E1-covalently linked to labeled ubiquitin is shown by the indicated high molecular weight band. In FIG. 9B, bands indicating ubiquitinated E1 and E2 (UBC5c) are shown in lane 1, and this ubiquitination is not present in lane 2 (reaction performed in the absence of E1) or lane 3 (reaction performed in the presence of DTT). FIG. 9C shows ubiquitinated E1 and E2 (UBC7) in lane 1, and this ubiquitination is not present in lane 2 (reaction performed in the absence of E1) or lane 3 (reaction performed in the presence of DTT).

FIGS. 10A-10C are autoradiograms illustrating the ubiquitination of the HECT E3 ligase WWP1 WW domain in a coupled ubiquitination assay. In each Figure, incorporation of labeled ubiquitin into a WWP1 HECT domain containing residues 611-985 or 611-990 is shown, as indicated. Reactions were performed in the presence or absence of DTT, as indicated. Ubiquitinated WWP1-GST is indicated by the arrow. In FIG. 10A the E2 was UBC5c, and in FIG. 10B the E2 was UBS7. Controls (FIG. 10C) were performed in the absence of E2.

In FIG. 11A the E2 was UBC5c, and in FIG. 11B the E2 was UBS7. Controls (FIG. 11C) were performed in the absence of E2 (lane 1) or in the absence of E1 and E2 (lane 2).

FIGS. 12A-12C are autoradiograms illustrating the time course of ubiquitination of the HECT E3 ligase WWP1 in a coupled ubiquitination assay. In each Figure, incorporation of labeled ubiquitin into a WWP1 HECT domain containing residues 611-985 following various incubation times, as indicated, is shown. In FIG. 12A the E2 was UBC5c, and in FIG. 12B the E2 was UBS7. A control (FIG. 12C) was performed in the absence of E2, in a 60 minute reaction.

DETAILED DESCRIPTION OF THE INVENTION

As noted above, the present invention is generally directed to methods for identifying agents that modulate signaling mediated by one or more TGF-β family members (e.g., transforming growth factor beta (TGF-β) or bone morphogenic protein (BMP)), and to methods for using such agents for therapeutic purposes. The agents identified using the methods provided herein generally modulate such signaling by targeting specific Smad proteins inside cells. Such agents provide a powerful way to alter the response of cells to TGF-β family members.

The present invention is based, in part, on the discovery that signaling mediated by TGF-β family members is dampened by ubiquitin-mediated degradation of certain Smad proteins (such as Smad1 and Smad5 for BMP, or Smad2 and Smad3 for TGF-β). The ubiquitin-mediated degradation is generally induced by the TGF-β family members(s) involved in triggering signaling. Further, it has been found within the context of the present invention that HECT E3 ubiquitin ligases that contain a WW domain bind to a PY motif in certain Smad PY proteins, resulting in ubiquitination and proteasome-mediated degradation of the target Smads. Agents that inhibit binding between a HECT E3 WW domain and a Smad PY motif may generally be used to inhibit degradation of a Smad protein (i.e., stabilize the Smad protein), resulting in enhanced TGF-β family member-mediated signaling.

Figure 1:
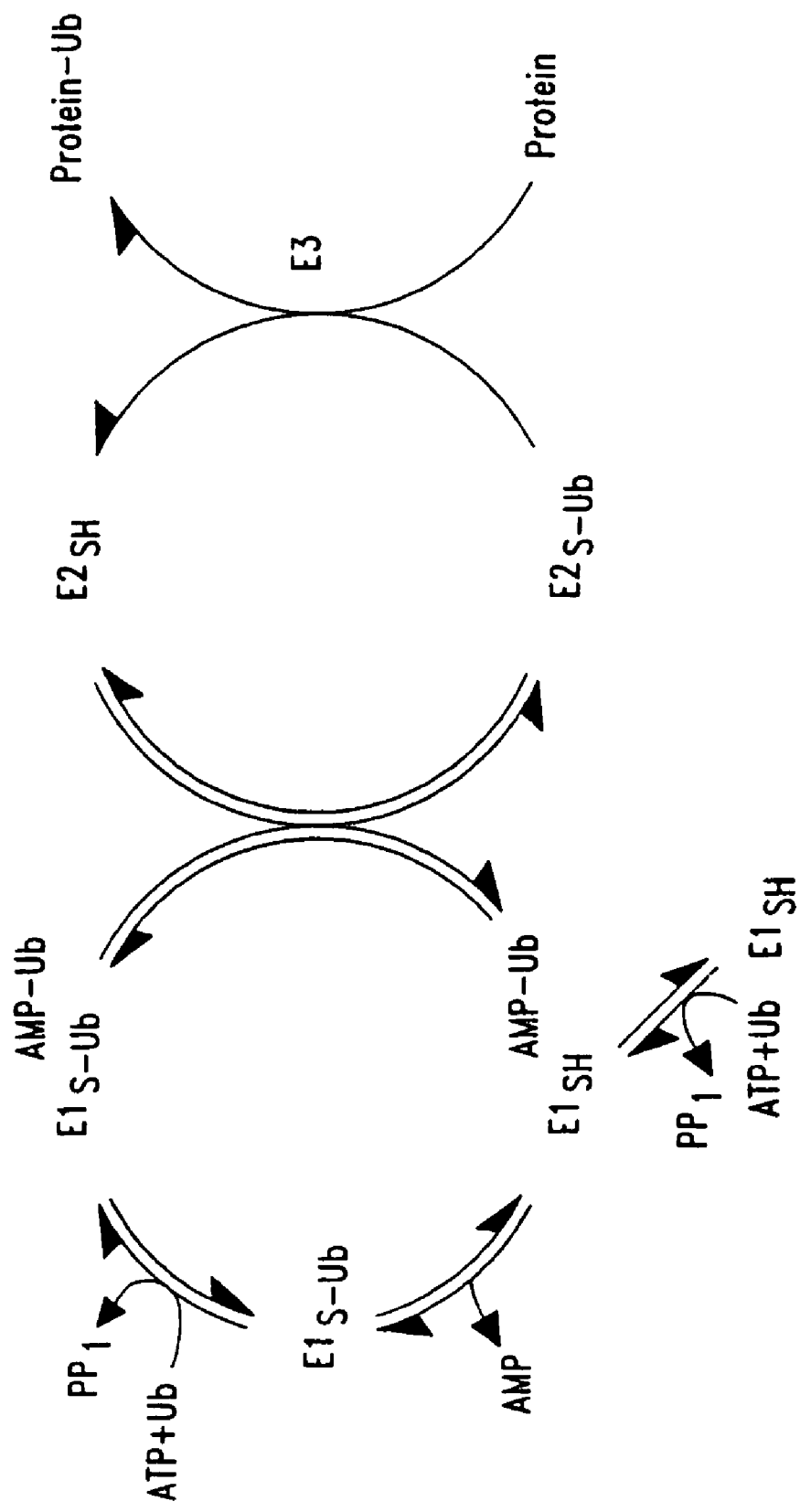
FIG. 1 is a diagram illustrating the general mechanism for ubiquitin (Ub) ligation to targeted proteins. Ubiquitination is initiated by ATP-dependent transfer of a ubiquitin monomer to enzyme 1 (E1) in the ubiquitin cascade. Following ubiquitin activation on E1, a transfer of ubiquitin to a ubiquitin carrier protein (E2) occurs. Transfer of the ubiquitin to a targeted protein is mediated by ubiquitin ligases (E3's).

Ubiquitin-mediated protein degradation is regulated by the ubiquitin conjugating pathway (FIG. 1). Within this pathway, selective ubiquitination is indicated by ATP-dependent transfer of a ubiquitin monomer to enzyme 1 (E1) in the ubiquitin cascade. Ubiquitin bound to E1 is then activated with ATP to form an ubiquitin-AMP intermediate. The AMP is displaced by the E1 active site cysteine to form a thioester linkage with the carboxy terminus of ubiquitin. A second activated ubiquitin is then formed by E1, which allows the E1 to transfer ubiquitin from its active site cysteine to the active site cysteine of a ubiquitin carrier protein (E2). During this transfer, diversity in the ubiquitination pathway begins to initiate and amplify. The greatest degree of selectivity in the ubiquitination cascade occurs at the level of ubiquitin transfer, ligation and polymerization on selected substrates. This terminal step is mediated by ubiquitin ligases (E3's). E2 either transfers the ubiquitin from its active site to the cysteine of an E3 ubiquitin ligase or to the target protein in an E3-dependent manner. Following transfer and ligation of the ubiquitin onto substrates by E3, the ubiquitinated protein is targeted for degradation by the 26S proteasome. Selectivity for proteasome-mediated protein degradation is determined by the ubiquitin tag.

As used herein, a HECT E3 ubiquitin ligase is an E3 ubiquitin ligase that contains a HECT (Homologous to E6 Carboxyl Terminus) sequence within the catalytic carboxy-terminal domain. Preferred HECT sequences satisfy the following consensus sequence:

(SEQ ID NO:1)
(Y/F)X$_{(2-3)}$YX$_{(8-11)}$WFWXI(V/I/L)X$_5$EX(K/R)X$_3$(L/V)QF(V/L)TG(T/S)XRLP (L/V/M/A/I)XGFXXLX$_{(4-10)}$IX$_{(7-9)}$LPXXHTCFNXLDLPXYXSX$_3$(L/M)X$_2$ (R/K)LX$_2$AIX$_{(4-6)}$F wherein X=any amino acid; (Y/F)=Y preferred over F.

E3 ubiquitin ligases are members of the ubiquitination cascade that transfer ubiquitin to specific substrates, rendering the substrates targets for proteasome-mediated degradation. Known HECT E3 ubiquitin ligases include, for example, WWP1 (Pirozzi et al., J. Biol. Chem 272:14611-16, 1997), E6-associated protein (E6-AP; Huibregtse et al., Mol. Cell. Biol. 13.775-84, 1993), Rsp5 (Huibregtse et al., Proc. Natl. Acad. Sci. USA 92:2563-67, 1995) and Nedd4 (Staub et al., EMBO J. 15:2371-80. 1996). Other HECT E3 ubiquitin ligases may be identified based on sequence similarity to known proteins and/or the presence of functional properties of HECT E3 ligases. A variety of techniques may be used to evaluate sequence similarity. One such technique is searches of sequence databases (e.g., GENBANK™). Such searches may be performed using well known programs (e.g., NCBI BLAST searches), and proteins that display high levels of sequence identity and/or similarity are candidate HECT E3 ligases. Alternatively, techniques employing low stringency hybridization may facilitate the identification of a HECT E3 ligase. Within such techniques, a known HECT E3 ubiquitin ligase (or a portion thereof) is used as a probe to screen a library (cDNA or genomic) for hybridizing sequences. Suitable low stringency hybridization conditions include, but are not limited to, 1.0×SSPE or SSC, 0.1% SDS, 50° C. Yet another technique for evaluating sequence similarity employs PCR reactions that are performed using degenerate primers that encode a conserved sequence.

Alternatively, or in addition, a functional assay may be used to identify a HECT E3 ubiquitin ligase. Certain assays detect binding to substrates, such as Smad proteins or portions thereof (e.g., portions comprising a PY motif as described herein). Such assays are well known in the art, and include affinity purification, yeast two-hybrid screens and screens of phage display libraries. Methods for performing these and other binding assays are amply described in the patent and scientific literature (e.g., Sambrook et al., *Molecular Cloning: A Laboratory Manual*, Cold Spring Harbor Laboratories, Cold Spring Harbor, N.Y., 1989; Brachman and Boeke, *Current Opinion in Biotechnology* 8:5661-568, 1997; and references cited therein). Other functional assays may be designed to assess ubiquitin transferring activity of a candidate HECT E3 ubiquitin ligase. Such assays may be performed using known techniques (e.g., coupled ubiquitin assays or ubiquitin dependent proteolysis assays in which the activity of E3 for transferring ubiquitin to a substrate is coupled with a measurement of substrate proteolysis), which are described in greater detail below. A HECT E3 ubiquitin ligase should display detectable ubiquitin transferring activity within such assays.

A Smad protein is a protein that is homologous to a known Smad protein (i.e., displays at least 50% primary sequence identity in the MH2 domain), and that participates in signal transduction mediated by a TGF-β family member (i.e., expression of a Smad protein detectably enhances or inhibits such signal transduction as measured using any assay suitable for the particular TGF-β family member). Smad proteins of particular interest include Smad1 (Hoodless et al., Cell 89:1165-1173, 1996), Smad2 (Nakao et al., J. Biol. Chem 272:2896-2900, 1997), Smad3 (Zhang et al., Nature 383:168-172, 1996), Smad5 (Liu et al., Nature 381:620-623, 1996), Smad6 (Imamura et al., Nature 389:622-626, 1997) and Smad7 (Hayashi et al., Cell 89:1165-1173, 1997). It will be apparent, however, that any Smad protein that contains a PY motif as described herein may be stabilized using the methods provided herein.

Assays for Agents That Modulate TGF-β Family Member-Mediated Signaling

Screening assays for agents that modulate TGF-β- and/or BMP-mediated signaling, or signaling mediated by one or more other TGF-β family members, may be performed in a variety of formats, including cell-based and in vitro assays. In general, such an assay should evaluate the effect of an agent on: (1) binding of a HECT E3 ubiquitin ligase WW domain to Smad PY motif; (2) ubiquitination of a Smad protein by E3 ubiquitin ligase; (3) proteolysis of a Smad protein (e.g., by assessing the cellular level of a Smad protein) or (4) HECT E3 ubiquitin ligase activity. For assays involving Smad proteins, agents that modulate BMP-mediated signaling may be identified through the use of Smad1 or Smad5 (or a variant of Smad1 or Smad5). Similarly, agents that modulate TGF-β-mediated signaling may be identified through the use of Smad2 or Smad3 (or a variant of Smad2 or Smad3).

Candidate agents that may be screened within the assays provided herein include, but are not limited to, antibodies and antigen-binding fragments thereof, competing peptides that correspond to a WW domain or PY motif, and other natural or synthetic molecules, such as small molecule inhibitors, that bind to a HECT E3 ubiquitin ligase or Smad protein. Candidate agents may be present within a library (i.e., a collection of compounds). Such agents may, for example, be encoded by DNA molecules within an expression library. Other such agents include compounds known in the art as "small molecules," which have molecular weights less than $10^5$ daltons, preferably less than $10^4$ daltons and still more preferably less than $10^3$ daltons. Such candidate agents may be provided as members of a combinatorial library, which includes synthetic agents (e.g., peptides) prepared according to multiple predetermined chemical reactions. Those having ordinary skill in the art will appreciate that a diverse assortment of such libraries may be prepared according to established procedures, and members of a library of candidate agents can be simultaneously or sequentially screened as described herein.

In vitro assays may be used for rapid screening of candidate agents for the ability to inhibit binding of a HECT E3 ubiquitin ligase to a Smad protein. As noted above, this binding has been found, within the context of the present invention, to take place between the WW domain of HECT E3 ubiquitin ligase and the PY motif of certain Smad proteins. Accordingly, any in vitro assay that assesses the effect of a candidate agent on this interaction may be used to identify agents that modulate TGF-β family member-mediated signaling (i.e., signaling mediated by one or more members of the TGF-β family, including TGF-β, BMP, activin(s) and/or inhibin(s)). Such assays typically assess the affect of an agent on binding between a polypeptide comprising a HECT E3 WW domain, or a variant thereof, and a polypeptide comprising a Smad PY motif, or a variant thereof.

A HECT E3 WW domain, as used herein, is a region of a HECT E3 ubiquitin ligase that contains two tryptophan residues 20 to 22 amino acid residues apart (see M. Sudol, Prog. Biophys. Molec. Biol. 65:113-132, 1996), and detectably binds to a Smad PY motif, as described herein. Within preferred embodiments, a WW domain satisfies the following consensus sequence.

GPLPXGWEX$_3$tttGtXYYhXHNTtTTtWXtPt (SEQ ID NO:2)

wherein each t is an independently selected polar amino acid residue (e.g., S, H, P, D, E, T or Y), h is a hydrophobic residue (e.g., I, V, L or M) and X is any amino acid. Within this and other sequences provided herein, amino acid residues are indicated using the standard one or three-letter code.

Representative HECT E3 ubiquitin ligase WW domains include: SPLPPGWEERQDILGRTYYVNHESR-RTQWKRPTPQDNL (human Nedd4; SEQ ID NO:3), SGLPPGWEERQDILGRTYYVNHESR-RTQWKRPTPQDNL (human Nedd4; SEQ ID NO:4), GFLPKGWEVRHAPNGRPFFIDHNT-KTTTWEDPRKKIPA (human Nedd4; SEQ ID NO:5), GPLPPGWEERTHTDGRIFYINHNI-KRTQWEDPRLENVA (human Nedd4; SEQ ID NO:6), GRLPPGWERRTDNFGRTYYVDHNTRTTT WKRPTLDQTE (yeast Rsp5; SEQ ID NO:7); GELPSG-WEQRFTPEGRAYFVD HNTRTTTWVDPRRQQYI (yeast Rsp5; SEQ ID NO:8); GPLPSGWEMRLTNTARVY-FVDHNTKTTTWDDPRLPSSL (yeast Rsp5; SEQ ID NO:9); LPSGWGWEQRKDPHGR-TYYVDHNTRTTTWERPQPLPPG (SEQ ID NO:10; WWPI WW domain 1); QPLPPGWERRVDDRRRVYY-DHNTRTTTW QRPTMESVR (SEQ ID NO:11; WWPI WW domain 2); GLPPGWEKRVDSTDRVYFVNHNTKT-TQWEDPRTQGLQ (SEQ ID NO:12; WWPI WW domain 3) and EPLPEGWEIRYTREGVRYFVDHNTRTTTFK DPRNGKSS (SEQ ID NO:13; WWPI WW domain 4). Within the assays provided herein, a polypeptide comprising a WW domain may be a full length HECT E3 ubiquitin ligase, a portion thereof that comprises a WW domain, or a variant of such a polypeptide in which the WW domain is modified by one or more substitutions, additions, insertions and/or deletions such that the ability of the variant to bind to a Smad PY motif is not substantially diminished (i.e., is enhanced, unchanged or diminished by no more than 10%), relative to the native WW domain sequence. This binding activity may be assessed using a representative binding assay provided herein.

A Smad PY motif is a 10-14 consecutive amino acid portion of a Smad protein that contains a PPxY (Pro-Pro-Xaa-Tyr; SEQ ID NO:14) sequence, in which x and Xaa both represent any amino acid. Such a PY motif further binds detectably to a HECT E3 ubiquitin ligase WW domain, as provided herein. Representative Smad PY motifs are present, for example, within Smads 1, 2, 3, 5, 6 and 7.

Smad PY motifs preferably satisfy the consensus sequence Ser/Thr-Pro-Pro-Pro-Pro/Ala/Gly-Tyr (SEQ ID NO:15), wherein Ser/Thr is an amino acid residue that is serine or threonine and Pro/Ala/Gly is an amino acid residue that is selected from the group consisting of proline, alanine and glycine. For Smads 1 and 5 (which are involved in BMP-mediated signal transduction) a PY motif comprises the sequence TPPPAY (SEQ ID NO:16), preferably PADTPP-PAY(L/M)PPPD (SEQ ID NO:17). For Smads 2 and 3 (which are involved in TGF-β-mediated signal transduction) a PY motif comprises the sequence TPPPGY (SEQ ID NO:18), preferably TPPPGY(I/L)SEDG (SEQ ID NO:19). Polypeptides comprising a Smad PY motif may comprise, for example, a sequence such as ELESPPPPYSRYPM (SEQ ID NO:20), GPESPPPPYSRLSP (SEQ ID NO:21), PADT-PPPAYLPPED (SEQ ID NO:22), PADTPPPAYMPPDD (SEQ ID NO:23), IPETPPPGYISEDG (SEQ ID NO:24) or AGLTPPPGYLSEDG (SEG ID NO:25). Within the assays provided herein, a polypeptide comprising a PY motif may be a full length Smad protein, a portion thereof that comprises a PY motif, or a variant of such a polypeptide in which the PY motif is modified by one or more substitutions, additions, insertions and/or deletions such that the ability of the variant to bind to a HECT E3 ubiquitin ligase WW domain is not substantially diminished (i.e., is enhanced, unchanged or diminished by no more than 10%), relative to the native PY motif sequence. This binding activity may be assessed using a representative binding assay provided herein.

Preferably, a WW domain or PY motif polypeptide variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. Variants may also (or alternatively ) be modified by, for example, the deletion or addition of amino acids that have minimal influence on the secondary structure and hydropathic nature of the polypeptide.

WW domain and PY motif polypeptides may comprise additional sequences that are unrelated to an endogenous protein. Such sequences include signal (or leader) sequences at the N-terminal end of the protein that co-translationally or post-translationally direct transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

The WW domain polypeptide and PY motif polypeptide are contacted under conditions that permit binding between the two polypeptides in the absence of a candidate agent.

Candidate agent may be added to the reaction mixture before or after contact of the WW domain polypeptide with the PY motif polypeptide. The reaction is then incubated, and binding of the WW domain polypeptide to the PY motif polypeptide is assessed, using any standard technique. One suitable binding assay employs a solid support, as described above, to which one of the polypeptides is attached. Binding may be assessed by removing unbound substances and detecting the presence of the other polypeptide on the solid support. Such detection may be achieved using, for example, an antibody or antigen-binding fragment detection reagent, or using a competitive assay with labeled polypeptide, as described above. Alternatively, the polypeptide that is not immobilized on the support may itself comprise a tag that facilitates detection of bound polypeptide. Tags include, but are not limited to, biotin, enzymes, radioactive groups (e.g., $^{32}P$), dyes, luminescent groups, fluorescent groups and other sequences that are readily bound by a detection reagent (e.g., antigenic sequences specifically bound by particular antibodies). In general, an agent should detectably modulate binding between the WW domain polypeptide and PY motif polypeptide.

By way of example, one polypeptide (i.e., a WW domain polypeptide or PY motif polypeptide) may be immobilized through non-specific interactions (e.g., to a polystyrene plate) or through a protein tag interaction (e.g, an interaction between a $His_6$-fusion protein and a nickel plate). The polypeptide may be immobilized by, for example, contacting a polystyrene assay plate (Costar) with the polypeptide overnight at 4° C. in a 200 mM carbonate buffer (Pierce, Rockford Ill.) at a concentration ranging from 0.3 to 30 µg/mL. Unbound polypeptide may be removed by washing with distilled, deionized water and the plates may then be blocked with 1% BSA/carbonate buffer for two hours at room temperature. Plates may then be washed with Tris/TWEEN® buffer (50 mM Tris pH 7.5, 100 mM NaCl, 1 mM EDTA, 1% BSA, 1 mM DTT 0.1% TWEEN®20 detergent, protease inhibitor cocktail (Boehringer-Mannheim). The other polypeptide may be labeled (e.g., biotinylated) and allowed to bind to the immobilized polypeptide (e.g., solvated in Tris/TWEEN® buffer and incubated in the assay plates at 4° C. for varying amounts of time). Plates may then be washed with PBS/0.1% TRITON® X-100 detergent. Binding may be detected by, for example, probing the assay wells with 1 µg/mL Europium-labeled streptavidin (DELFIA; Wallac Oy, Turku, Finland) in DELFIA Assay Buffer/0.1% TRITON® X-100 for one hour at room temperature. Unbound Europium-labeled streptavidin may be removed by washing with PBS/0.1% TRITON® X-100 detergent. Europium may be released for time-resolved fluorescence (TRF) measurements with the DELFIA Enhancement Buffer. TRF measurements may be made, for example, with a DELFIA 1234 (Wallac Oy, Turku, Finland) fluorometer.

Within similar assays, a radioactive label may be substituted for the biotin. For example, a $^{32}P$-labeled polypeptide may be generated by phosphorylation of a suitable site linked to the WW domain polypeptide or PY motif polypeptide. One such site is the PKA site in the pGEX KG vector (Pharmingen), which may be labeled using $\alpha$-$[^{32}P]$-ATP and protein kinase A (Sigma). The amount of binding may be quantitated by, for example, Cerenkov counting or SDS-PAGE using standard techniques. The solid support used may also be varied. One suitable support for such assays is neutravidin agarose beads (Pierce, Rockford, Ill. ). Binding may be performed using such a support by incubation in a PBS/1% TWEEN° 20 detergent buffer in an end-over shaker at 4° C. for varying amounts of time. It will be apparent that any of these assays may be modified to permit immobilization after binding takes place.

To determine the effect of a candidate agent on binding of the WW domain to the PY motif, the level of binding is compared in the presence and absence of candidate agent. An agent that detectably inhibits or enhances such binding may be used to alter TGF-β family member-mediated signaling in a cell. Preferred agents modulate TGF-β and/or BMP-mediated signaling.

Other in vitro assays may be designed to assess the affect of an agent on ubiquitination of an E3 ubiquitin ligase and/or a Smad. In vitro ubiquitination reactions are well known in the art. For example, coupled ubiquitination assays (in which ubiquitin transfer from E1 to E2, and from E2 to E3, is monitored) may be employed. Such assays require the reconstitution of an E1/E2/E3 pathway. Recombinant E1 and E2 components are available from a variety of sources (e.g., BostonBiochem, Cambridge, Mass.) for coupling ubiquitin to an E3 ligase of interest. Radiolabeled ubiquitin may be generated using standard techniques, such as PKA-mediated incorporation of $[^{32}P]$-phosphate from $\alpha$-$[^{32}P]$-ATP to the PKA site of the GST-ubiquitin fusion protein (pGEX KG expression vector). One suitable ubiquitin assay buffer is: 50 mM Tris pH 7.6, 1 mM ATP, 0.2 mM EDTA, 5 mM $MgCl_2$, 1 unit inorganic pyrophosphatase, 0.005% TRITON® X-100 detergent and 1 µM staurosporine. In a 0.030 mL reaction, the following amounts of reaction components are generally suitable: 50-200 ng E1, 0.1-1 µg E2, 5 µg GST-ubiquitin (BostonBiochem, Cambridge, Mass.) and 50-200 ng E3. Reactions may be performed at room temperature and terminated with a SDS-PAGE loading buffer that does not contain mercaptans. Reactions may be analyzed by SDS-PAGE. An assay may be similarly performed with endogenous proteins from, for example, HeLa cell extract fractions (see Hershko et al., J. Biol. Chem. 258:8206-8214, 1983). For measuring Smad protein ubiquitination, a Smad polypeptide is included in the reaction. These assays may be further modified to measure Smad protein degradation by incorporation of 100-1000 ng of 20S proteasome (Boston Biochem, Cambridge, Mass.) into the assay.

A Smad polypeptide for use within such an assay may be tagged to facilitate detection of covalently attached ubiquitin. Such a polypeptide may be a full length Smad protein, or may be truncated protein or a variant thereof, provided that the polypeptide contains a functional PY motif and ubiquitination site. A ubiquitination site may be identified based on criteria known in the art. For example, ubiquitination generally occurs on lysine residues within 100 amino acids of the HECT/WW binding site. Similarly, a HECT E3 ubiquitin ligase for use within such assays may be a full length protein, a truncated protein or a variant thereof, provided that the ligase contains a functional WW domain and HECT domain and ubiquitinates a Smad protein of interest.

Cell-based assays (i.e., assays in which intact cells are exposed to a candidate agent) may be used to detect the effect of an agent on Smad protein degradation in a cellular environment. Such assays may be performed using any cell that expresses a receptor for a TGF-β family member ligand. Within preferred embodiments, a cell expresses a TGF-β and/or bone morphogenic protein (BMP) receptor. Known BMP receptors include ALK2, 3 and 6 (see Attisano et al., *Cell* 68:97-108, 1992; ten Dijke et al., *Oncogene* 8:2879-2887, 1993). Known TGF-β and activin receptors have been described, for example, by Attisano et al., *Cell* 75:671-680, 1993; Attisano et al., *Mol. Cell Biol.* 16:1066-1073, 1996; Ebner et al., *Science* 262:900-902, 1993 Lin et al., *Cell* 68:775-785, 1992; Mathews and Vale; *Cell* 65:973-982, 1991; and Tsuchida et al., *Proc. Natl. Acad. Sci. USA* 90: 11242-11246, 1993. Suitable cells may be readily identified using immunochemical methods (employing antibodies raised against known BMP or TGF-β receptors), by direct measurement of BMP or TGF-β binding to the cells or by the detection of a BMP- or TGF-β-mediated response in the cells following exposure to BMP or TGF-β. Such methods are well known in the art. Preferred methods for identifying suitable cells involve the use of a reporter gene in which expression is under the control of a TGF-β or BMP response element. In general, a cell should express a level of receptor that is detectable using any such assay. Cells that express a BMP receptor include, but are not limited to, bone cells, neurons and kidney cells. TGF-β receptors are generally widely expressed.

A cell that expresses a TGF-β family member receptor is contacted with an amount of the TGF-β family member that is sufficient to result in a detectable level of TGF-β family member-mediated signaling in the cell, using an assay for gene expression mediated by the TGF-β family member that is appropriate for the particular cell type. Such assays may be based on the detection of enhanced expression of TGF-β family member-regulated genes, such as via a hybridization or amplification-based assay, or an assay for expression of a reporter gene operably linked to a TGF-β- or BMP-regulated promoter. Alternatively, such an assay may be a functional assay. For example, BMP treatment for 1-2 weeks stimulates differentiation of osteoblasts. Contact of such cells with BMP should be sufficient to result in differentiation, as detected by mineralization. In general, contact of a cell with 100 ng BMP for 2-24 hours is sufficient to result in a detectable level of BMP-mediated signaling in the cell.

To determine the effect of a candidate agent on TGF-β family member-mediated signaling, a cell is contacted with a TGF-β family member ligand as described above, and with a candidate agent. A cell may be contacted with both substances simultaneously or sequentially, in either order. The amount of agent employed will vary, depending on the type of agent and the specific assay used, but in general 1 to 50 µM of a candidate agent is sufficient. Within preferred embodiments, the TGF-β family member is TGF-β or BMP.

Following contact with TGF-β family member and the candidate agent, TGF-β family member-induced Smad protein degradation (preferably Smad1, 2, 3, 5, 6 or 7 degradation) is assessed. It will be apparent that any of a variety of assays may be used to assess Smad protein degradation including, but not limited to, assays that detect the level of: (1) a Smad protein; (2) ubiquitination of a Smad protein; or (3) HECT E3 ubiquitin ligase activity in the cell. In each type of assay (described in greater detail below), the level detected is compared with a level detected in the same type of cell, under the same conditions, but in the absence of candidate agent. A statistically significant difference in the signal detected in the presence of candidate agent, relative to the signal detected in the absence of candidate agent, indicates that the agent modulates TGF-β family member-mediated signaling in the cell.

To assess the level of a Smad protein, well known immunochemical methods may be employed. Such methods typically use an agent, such as an antibody or antigen-binding fragment thereof, that specifically binds to the Smad protein. To perform such assays, cells are generally lysed and the lysate (with or without pretreatment) is contacted with antibody under conditions that permit antigen-specific binding. Bound antibody is then detected by means of a suitable detection reagent.

There are a variety of assay formats that may be used to detect the level of a Smad protein in a cell lysate. See, e.g., Harlow and Lane, *Antibodies: A Laboratory Manual*, Cold Spring Harbor Laboratory, 1988. In one embodiment, an assay involves the use of binding agent immobilized on a solid support to bind to and remove the Smad protein from the remainder of the lysate. The bound Smad protein may then be detected using a detection reagent that contains a reporter group and specifically binds to the binding agent/Smad complex. Such detection reagents may comprise, for example, an antibody that specifically binds to the Smad protein. Alternatively, a competitive assay may be used, in which a Smad protein or portion thereof is labeled with a reporter group and allowed to bind to the immobilized binding agent after incubation of the binding agent with the lysate. The extent to which components of the lysate inhibit the binding of the labeled Smad polypeptide to the binding agent is indicative of the level of the Smad protein in the lysate.

A solid support for use in such assays may be any material known to those of ordinary skill in the art to which a binding agent may be attached. For example, the solid support may be a test well in a microtiter plate or a nitrocellulose or other suitable membrane. Alternatively, the support may be a bead or disc, such as glass, fiberglass, latex or a plastic material. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the binding agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time (typically between about 1 hour and about 1 day). In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

In certain embodiments, the assay is a two-antibody sandwich assay. This assay may be performed by first contacting an antibody that has been immobilized on a solid support, commonly the well of a microtiter plate, with the lysate, such that a Smad protein within the sample is allowed to bind to the immobilized antibody (e.g., incubation for 30 minutes at room temperature). Unbound sample is then removed from the immobilized Smad-antibody complexes and a detection reagent (preferably a second antibody capable of binding to a different site on the Smad protein) containing a reporter group is added. The amount of detection reagent that remains bound to the solid support is then determined using a method appropriate for the specific reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

The level of ubiquitination of a Smad protein may be readily determined based on the alteration in electrophoretic mobility of the ubiquitinated protein. Briefly, cells may be lysed and proteins present within the lysate may be separated by SDS-PAGE. A protein of interest may be detected by Western blot analysis. Ubiquitination results in a shift in the apparent molecular weight of the protein to the higher molecular weight region of the gel. Quantitative or semi-quantitative results may be obtained using labeled secondary antibodies, or other detection reagents known in the art.

HECT E3 ubiquitin ligase activity in the cell may be evaluated by any of a variety of ubiquitination assays commonly used in the art. Such assays typically employ a tagged target protein and/or labeled ubiquitin. Ligase activity is then assessed using, for example, a coupled ubiquitination assay as described herein. Such assays generally employ E3 ubiquitin ligase (generally within a lysate, or partially or substantially purified from a cell lysate) to ubiquitinate the tagged target protein. Using radiolabeled ubiquitin, for example, the amount of ubiquitination of target protein may be determined by scintillation counting following removal of unbound ubiquitin. Alternatively, the degradation of target protein may be directly assessed by SDS-PAGE resolution of the reactions and detection of the tag. Assays to detect ubiquitination and degradation of proteins are well known in the art, and representative assays are described herein.

In general, the effect of an agent on TGF-$\beta$ family member-mediated signaling may be determined based on its activity within the above assays. For Smads that enhance BMP-mediated signaling (including Smads 1 and 5), agents that inhibit Smad protein degradation may be used to augment BMP-mediated signaling. Similarly, agents that enhance degradation of such Smad proteins may be used to inhibit BMP-mediated signaling. For TGF-$\beta$-mediated signaling, agents that inhibit Smad2 and/or Smad3 protein degradation may be used to augment signaling, and agents that enhance degradation of such Smad proteins may be used to inhibit signaling. Agents identified using the screens provided herein may be used within a variety of therapeutic contexts, as described in further detail below.

Methods of Use For Agents That Modulate TGF-$\beta$ Family Member-Mediated Signaling Agents that modulate BMP-mediated signaling may be used for the prevention or treatment of conditions associated with insufficient or excess BMP-mediated signaling in certain cell types. In general, an agent that augments BMP-mediated signaling (e.g., inhibits binding of a HECT E3 ubiquitin ligase WW domain to a Smad1 or Smad5 PY motif) is useful for stimulating bone anabolism, as well as treating broken bones, osteoporosis and acute or chronic renal failure. Agents that inhibit BMP-mediated signaling may be used, for example, within therapies for cancer, inflammation, aging and infectious diseases.

Similarly, agents that modulate TGF-$\beta$-mediated signaling may be used for the prevention or treatment of conditions associated with insufficient or excess TGF-$\beta$-mediated signaling in certain cell types. In general, an agent that inhibits TGF-$\beta$-mediated signaling (e.g., enhances binding of a HECT E3 ubiquitin ligase WW domain to a Smad2 or Smad3 PY motif) is useful for treating cancer, inflammation, neurodegeneration and fibrosis.

For administration to a patient, one or more agents are generally formulated as a pharmaceutical composition, which may be a sterile aqueous or non-aqueous solution, suspension or emulsion, and which additionally comprises a physiologically acceptable carrier (i.e., a non-toxic material that does not interfere with the activity of the active ingredient). Any suitable carrier known to those of ordinary skill in the art may be employed in a pharmaceutical composition. Representative carriers include physiological saline solutions, gelatin, water, alcohols, natural or synthetic oils, saccharide solutions, glycols, injectable organic esters such as ethyl oleate or a combination of such materials. Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, antimicrobial compounds, chelating agents such as EDTA or glutathione, adjuvants (e.g., aluminum hydroxide), inert gases and/or preservatives. Compositions of the present invention may also be formualted as a lyophilizate. Pharmaceutical compositions may also contain other compounds, which may be biologically active or inactive.

The compositions described herein may be administered as part of a sustained release formulation (i.e., a formulation such as a capsule that effects a slow release of compounds following administration). Such formulations may generally be prepared using well known technology and administered by, for example, oral, rectal or subcutaneous implantation, or by implantation at the desired target site. Sustained-release formulations may contain a polypeptide, polynucleotide or modulating agent dispersed in a carrier matrix and/or contained within a reservoir surrounded by a rate controlling membrane. Carriers for use within such formulations are biocompatible, and may also be biodegradable; preferably the formulation provides a relatively constant level of release. The amount of active compound contained within a sustained release formation depends upon the site of implantation, the rate and expected duration of release and the nature of the condition to be treated or prevented.

Another delivery system for such agents is a colloidal dispersion system. Colloidal dispersion systems include macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). It has been shown that large unilamellar vesicles (LUV), which range in size from 0.2-4.0 μm can encapsulate a substantial percentage of an aqueous buffer containing large macromolecules. The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

To achieve cell or tissue specificity, agents may (in some instances) be administered topically. Other agents may be specific for a particular HECT E3/Smad protein interaction, and thus may have a specific target cell type or tissue. It may, however, be beneficial in certain instances to employ a targeting moiety to facilitate delivery of an agent to a desired site. A targeting moiety is any compound (e.g., a monoclonal or polyclonal antibody, a protein or a liposome) or cell that facilitates the delivery of the agent to a target cell or tissue, thereby increasing the local concentration of the agent. Targeting moieties include antibodies or fragments thereof, receptors, ligands and other molecules that bind to cells of, or in the vicinity of, the target tissue. An antibody targeting agent may be an intact (whole) molecule, a fragment thereof, or a functional equivalent thereof. Examples of antibody fragments are F(ab')2, —Fab', Fab and F[v] fragments, which may be produced by conventional methods or by genetic or protein engineering. Linkage is generally covalent and may be achieved by, for example, direct condensation or other reactions, or by way of bi- or multi-functional linkers. Targeting moieties may be selected based on the cell(s) or tissue(s) at which the agent is expected to exert a therapeutic benefit.

As noted above, patients that may benefit from treatment with an agent that modulates TGF-β and/or BMP-mediated signaling are those that are afflicted with (or at risk for developing) a condition associated with insufficient or excess TGF-β and/or BMP-mediated signaling in certain cell types. Such conditions may be diagnosed using criteria accepted in the art for the condition, or by in vitro analysis of Smad protein level.

Agents may be administered to a patient by any procedure that is appropriate for the condition to be treated including, for example, topical, oral, nasal, intrathecal, rectal, vaginal, sublingual or parenteral administration, such as subcutaneous, intravenous, intramuscular, intrasternal, intracavernous, intrameatal or intraurethral injection or infusion. As appropriate dosage and a suitable duration and frequency of administration will be determined by such factors as the condition of the patient, the type and severity of the patient's disease, the particular form of the active ingredient and the method of administration. In general, an appropriate dosage and treatment regimen provides the agent(s) in an amount sufficient to provide therapeutic and/or prophylactic benefit (e.g., an improved clinical outcome, such as more frequent complete or partial remissions, or longer disease-free and/or overall survival). For prophylactic use, a dose should be sufficient to prevent, delay the onset of or diminish the severity of a condition associated with TGF-β and/or BMP-mediated signaling. Optimal dosages may generally be determined using experimental models and/or clinical trials. The use of the minimum dosage that is sufficient to provide effective therapy is usually preferred. Patients may generally be monitored for therapeutic or prophylactic effectiveness using assays suitable for the condition being treated or prevented, which will be familiar to those of ordinary skill in the art. Suitable dose sizes will vary with the size of the patient, but will typically range from about 10 mL to about 500 mL for 10-60 kg animal.

The following Examples are offered by way of illustration and not by way of limitation.

EXAMPLES

Example 1

Ubiquitination of Smad Proteins and Initial Characterization of E3/Smad Protein Binding This Example illustrates the BMP-induced ubiquitination of Smad proteins, and the identification of a HECT E3 ligase domain that binds to Smad proteins.

Figure 2:
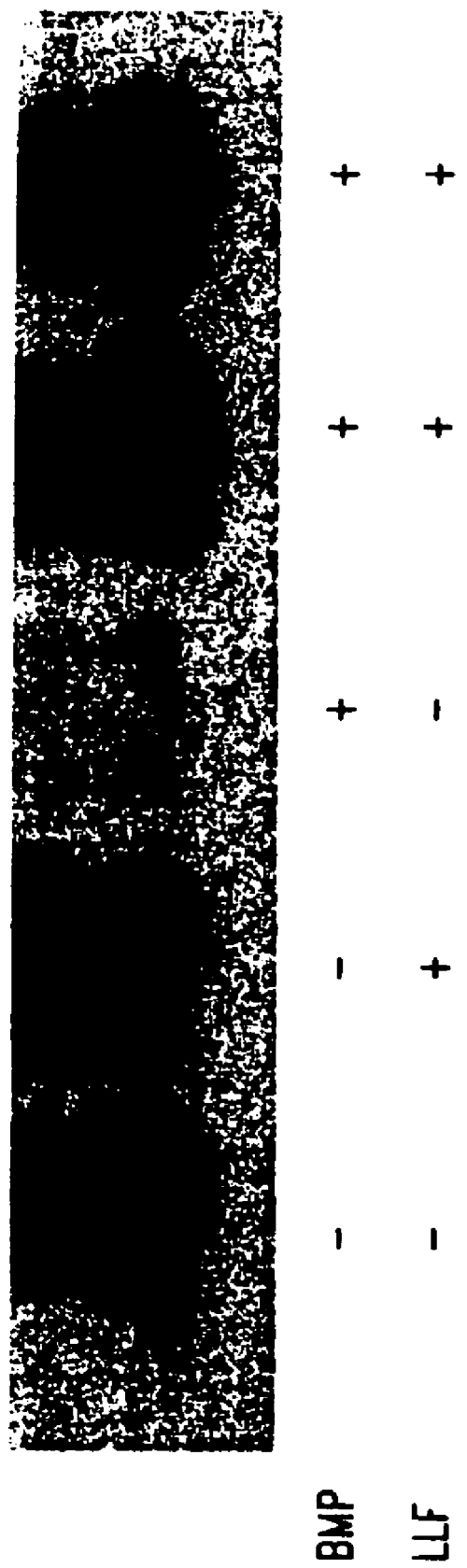
FIG. 2 is a Western blot illustrating the induction of Smad1 degradation by BMP. The level of tagged Smad1 in transfected cells following treatment with BMP and/or LLF (Leu-Leu-Phe, a proteasome inhibitor) is shown, as indicated.

HA-tagged Smad1 expression vector was transfected into COS cells. The transfected cells were then treated with 100 ng BMP for 4 hours in the absence or presence of 50-100 μM of the proteasome inhibitor Leu-Leu-Phe (LLF). The cells were lysed and equal amount of protein was loaded in each lane. Western analysis was performed using anti-HA antibody (BAbCo, Berkeley, Calif.). As shown in FIG. 2, BMP induces Smad1 degradation and LLF blocks BMP-induced Smad1 degradation.

Figure 3:
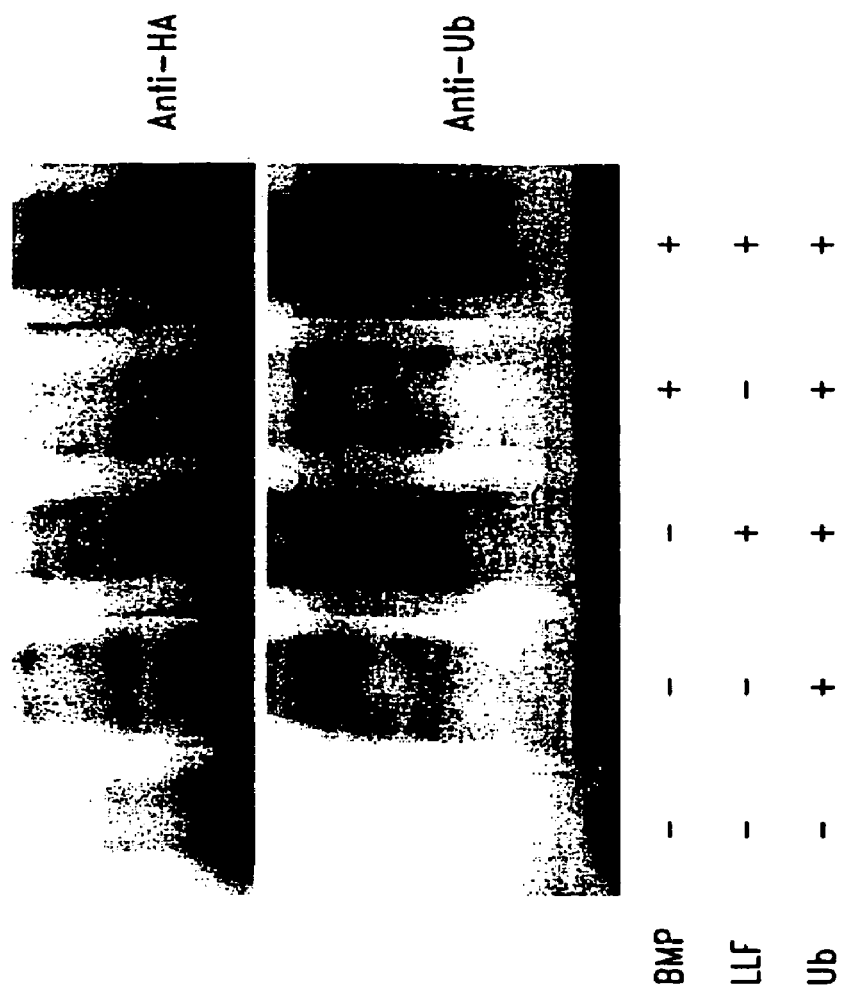
FIG. 3 is a Western blot illustrating Smad1 ubiquitination. COS cells expressing HA-tagged Smad1 were treated with one or more of BMP, LLF and/or ubiquitin (Ub), as indicated. Cells were lysed and Smad1 was immunoprecipitated. Western blots were probed with Anti-HA and anti-ubiquitin antibodies, as indicated.

To assess the in vivo ubiquitination of Smad1, a Smad1 expression vector was transfected into COS cells. The transfected cells were treated with BMP and the proteasome inhibitor LLF, as described above. The cells were then lysed and equal amounts of protein were used for immunoprecipitation using anti-HA antibody, to precipitate tagged-Smad1 protein. The immunoprecipitated Smad1 was run on SDS-PAGE, followed by a Western blot using anti-HA antibody or anti-ubiquitin antibody (BAbCo). Cells treated with LLF and cells treated with LLF plus BMP clearly accumulated more high molecular weight, ubiquitinated-Smad1 protein (FIG. 3).

Figure 4:
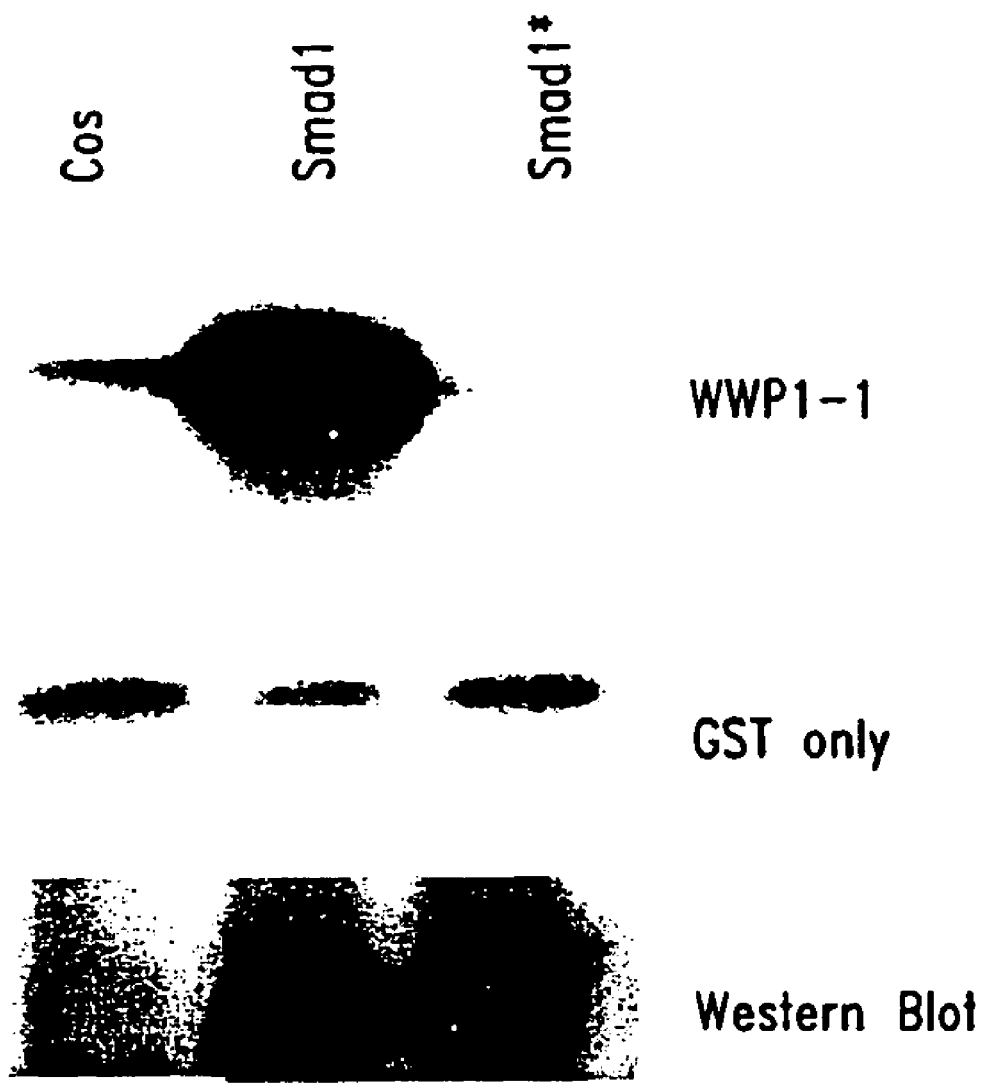
FIG. 4 is an autoradiogram illustrating the binding of WWP1.1 to the PY motif of Smad1. Untransfected COS cells (COS), or COS cells transfected with HA-tagged Smad1 or altered Smad1 with a mutated PY motif (Smad1*), were lysed. Smad1 was immunoprecipitated and incubated with $^{32}$P-labeled GST-fusion proteins of the WWP1.1 WW domain. Bound WWP1.1 was then detected autoradiographically, as indicated.
Figure 5A:
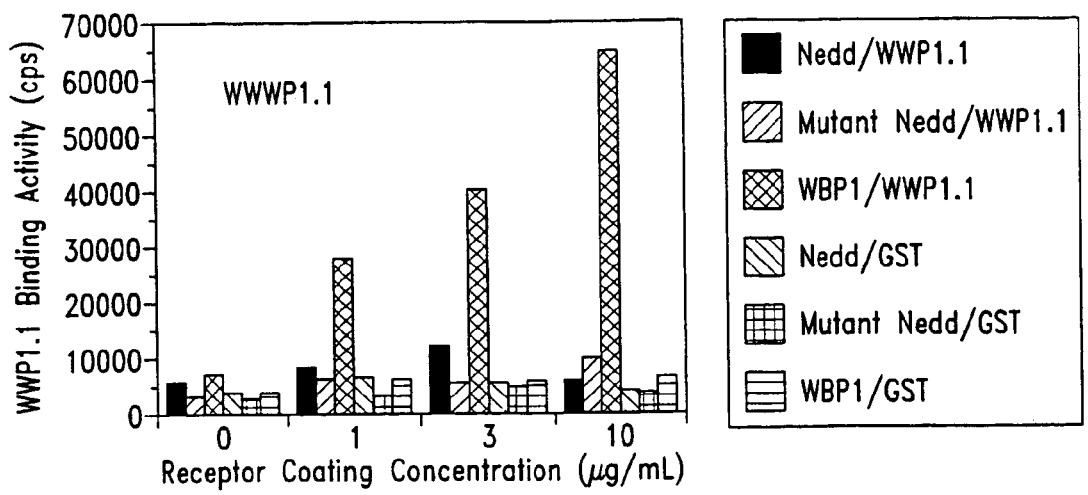
FIGS. 5A-5D are histograms illustrating the binding of PY motif peptides to WWP1 WW domain peptides. Four GST fusion peptides were assayed: GST-WWP1.1 (FIG. 5A), GST-WWP1.2 (FIG. 5B), GST-WWP1.3 (FIG. 5C) and GST-WWP1.4 (FIG. 5D). In each panel, binding to GST alone is also shown (cross-hatched columns, as indicated). WW domain peptides were coated on polystyrene plates at the indicated receptor coating concentrations, and blocked with BSA. Biotinylated PY motif peptides (Nedd, mutant Nedd and WBP1) were then added as indicated. Binding was assessed using a time-resolved fluorescence assay and is shown as binding activity (cps).
Figure 5B:
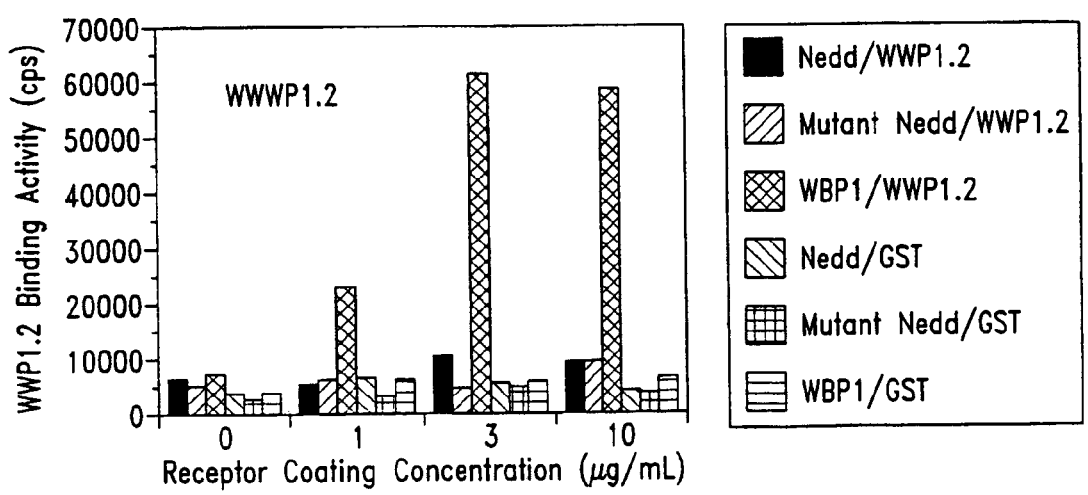
Figure 5C:
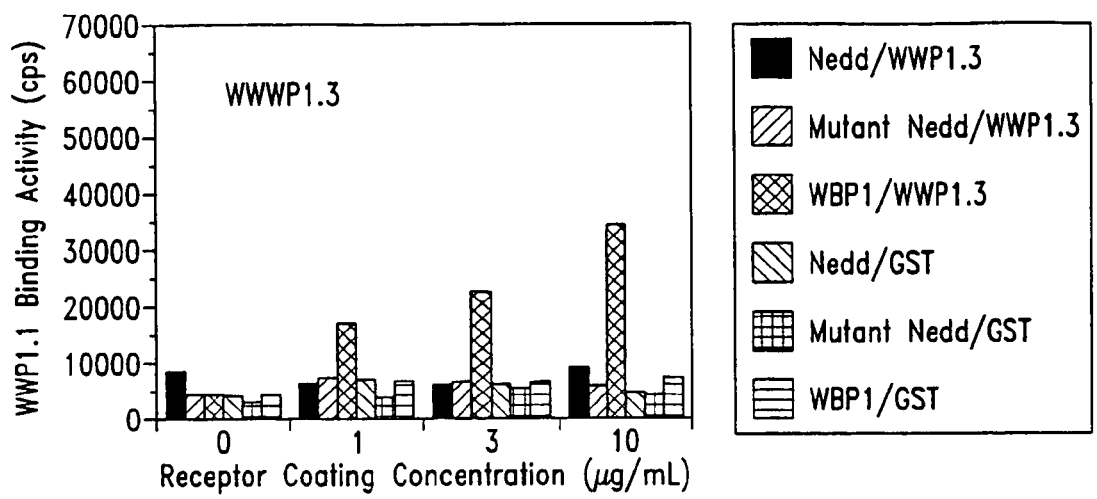
Figure 5D:
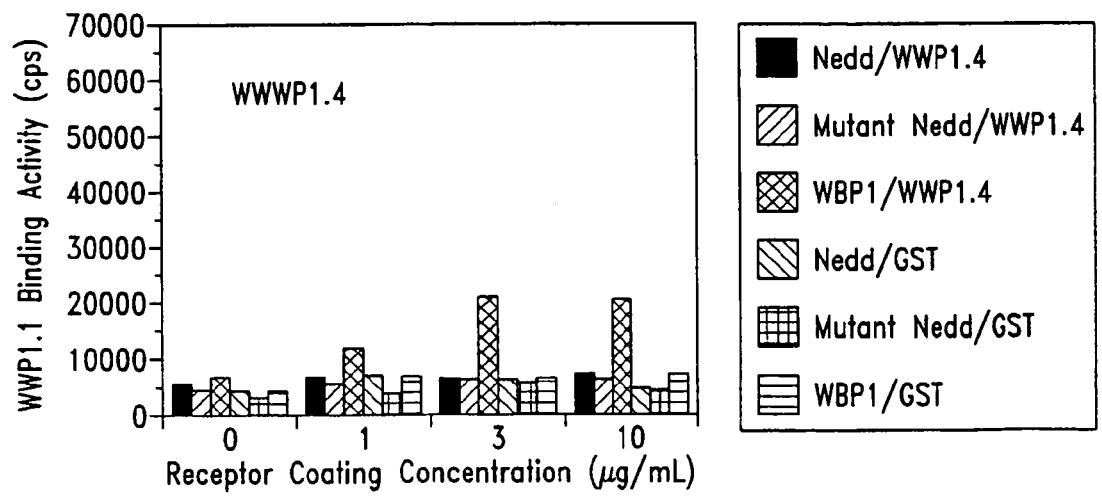
Figure 6A:
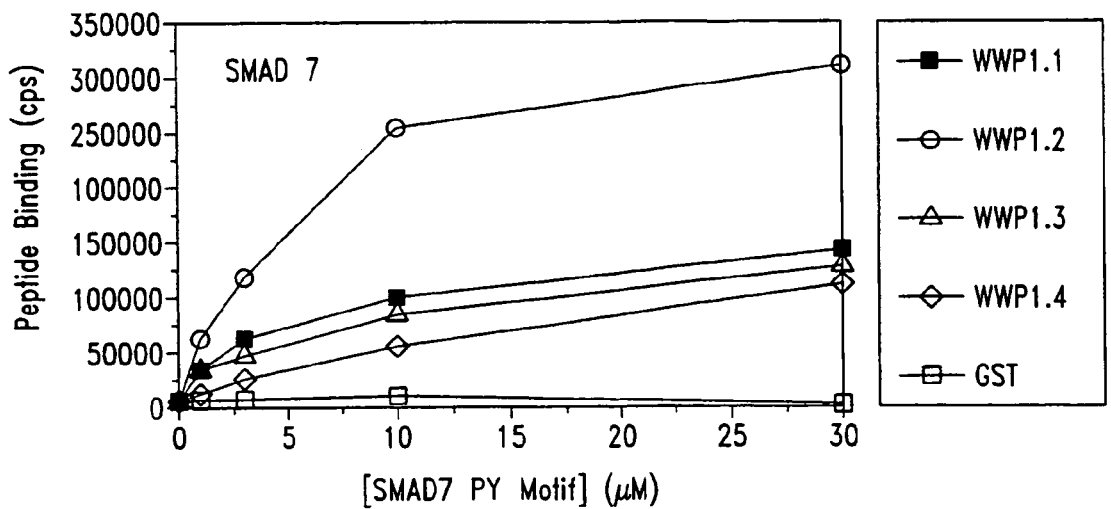
FIGS. 6A-6D are graphs illustrating the binding of Smad PY motif peptides to WWP1 WW domain peptides. Four GST fusion peptides were assayed, and are shown in each graph: GST-WWP1.1, GST-WWP1.2, GST-WWP1.3 and GST-WWP1.4. Binding to GST alone is also shown (open squares). WW domain peptides were coated on polystyrene plates at the indicated receptor coating concentrations, and blocked with BSA. Biotinylated PY motif peptides (Smad7 (FIG. 6A); Smad6 (FIG. 6B); Smad2 (FIG. 6C) and Smad3 (FIG. 6D) were then added as indicated. Binding was assessed using a time-resolved fluorescence assay and is shown as cps.
Figure 6B:
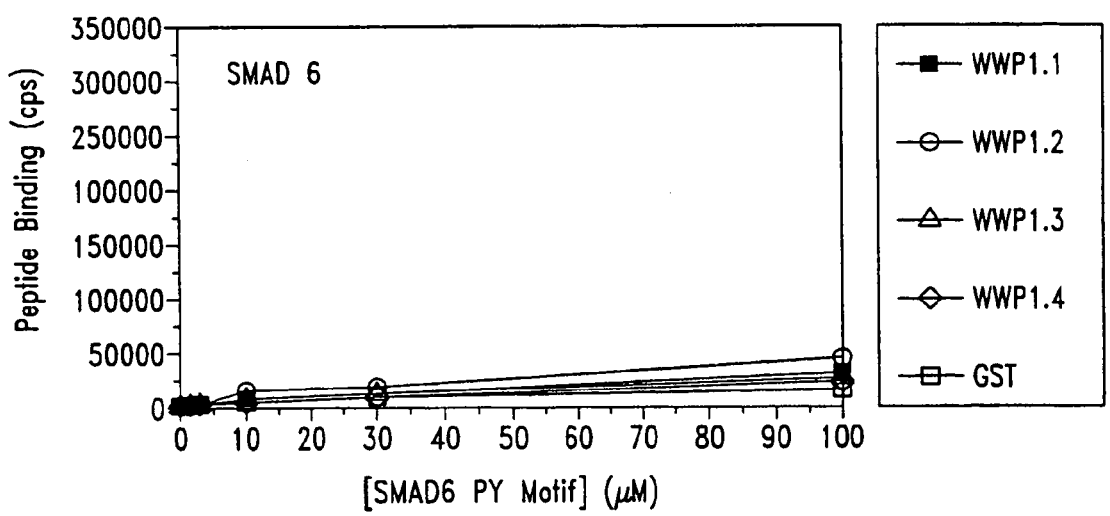
Figure 6C:
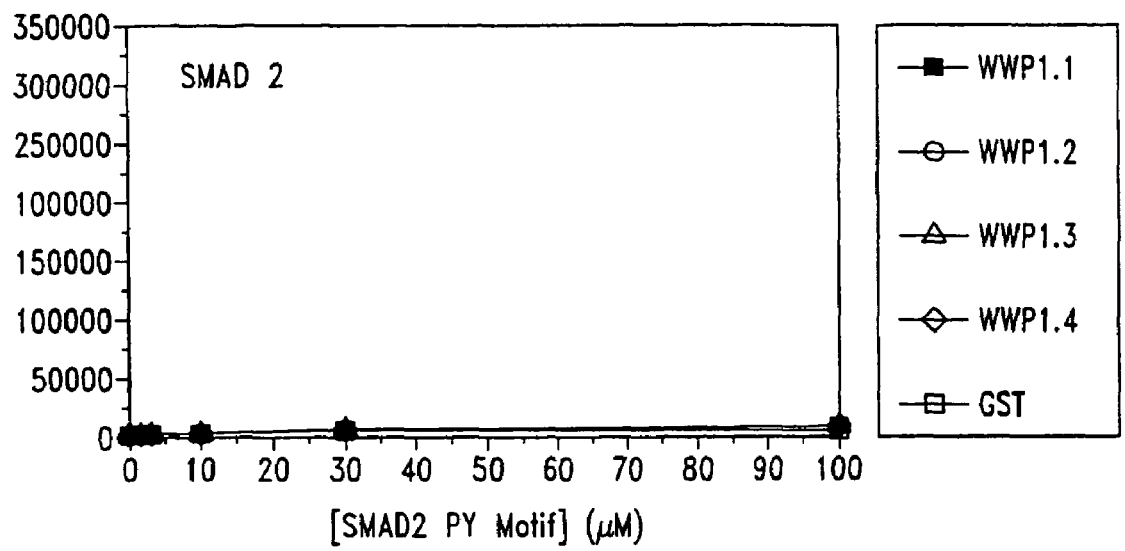
Figure 6D:
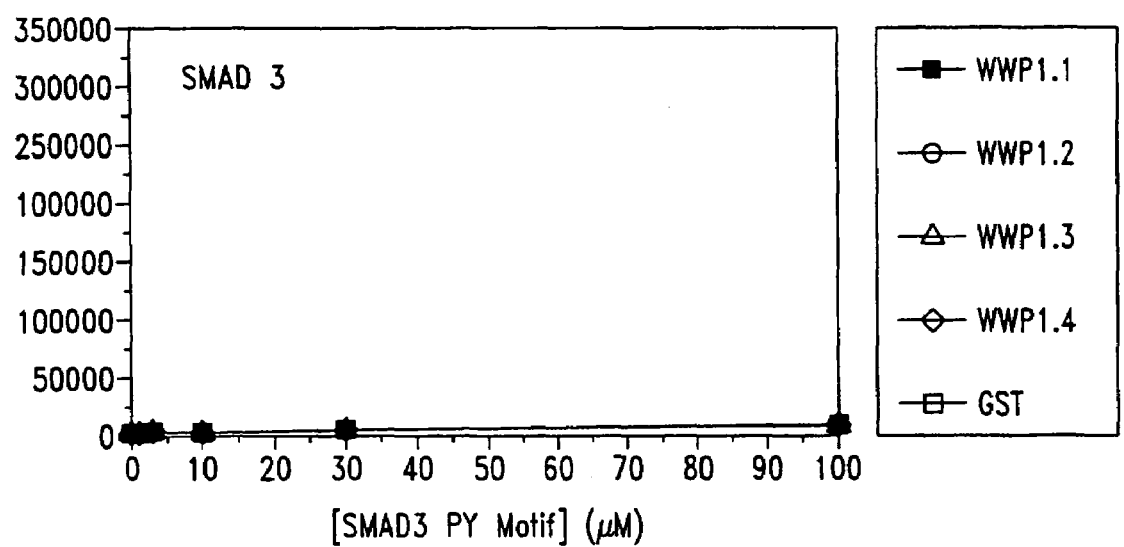
Figure 7A:
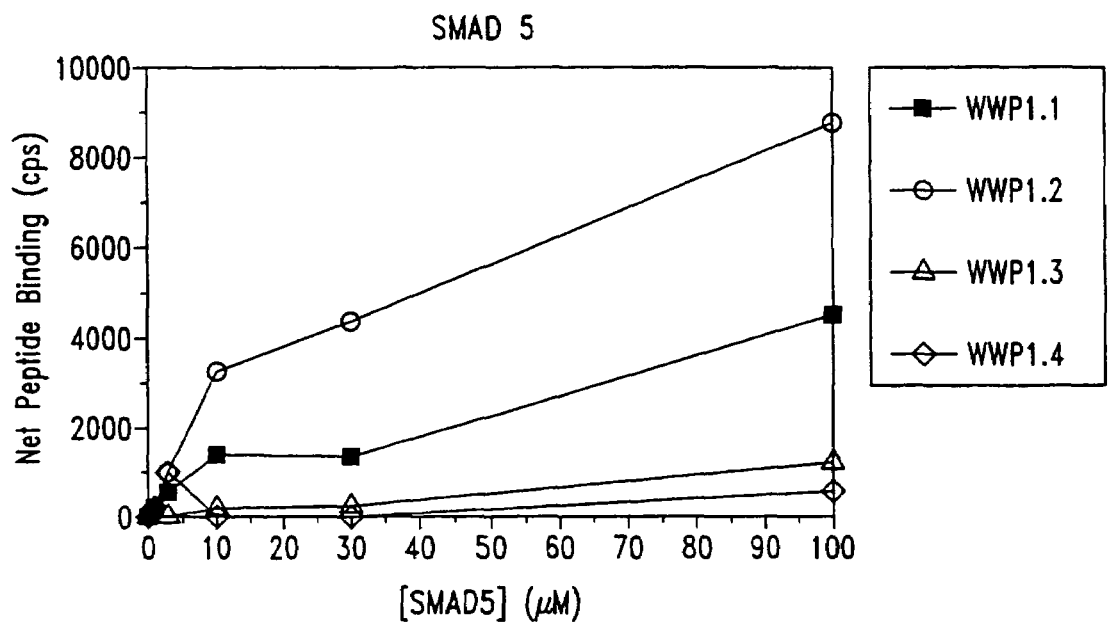
FIGS. 7A-7B are graphs illustrating the binding of Smad PY motif peptides to WWP1 WW domain peptides. Four GST fusion peptides were assayed, and are shown in each graph. GST-WWP1.1, GST-WWP1.2, GST-WWP1.3 and GST-WWP1.4. WW domain peptides were coated on polystyrene plates at the indicated receptor coating concentrations, and blocked with BSA. Biotinylated PY motif peptides (Smad5 (FIG. 7A) and Smad1 (FIG. 7B)) were then added as indicated. Binding was assessed using a time-resolved fluorescence assay and is shown as cps.
Figure 7B:
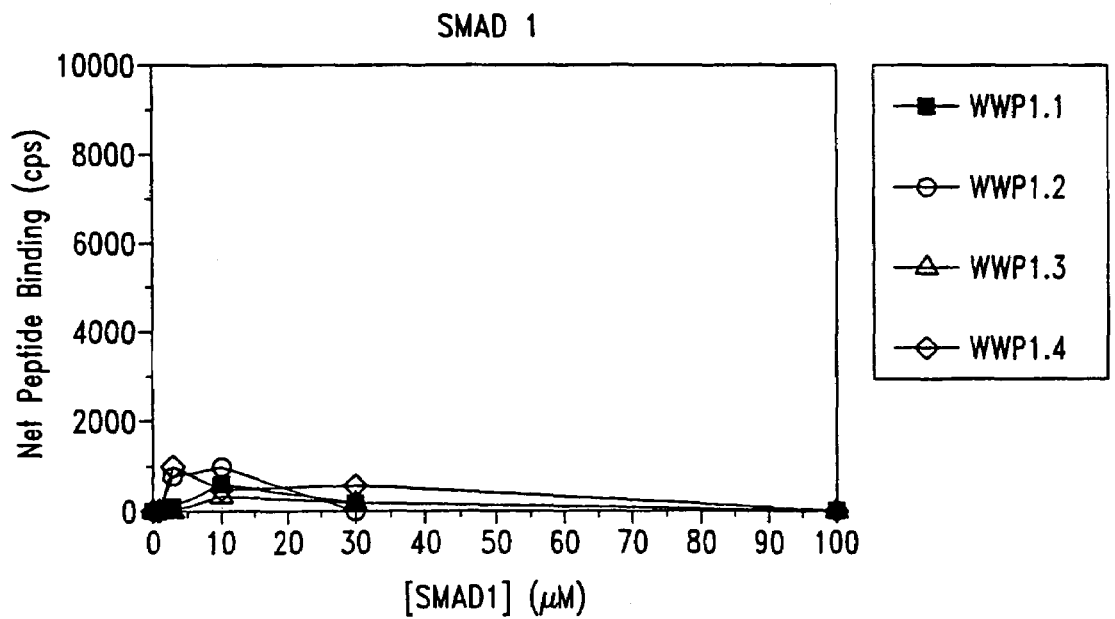

To analyze the in vitro binding of Smads with various WW domains, HA-tagged Smad1 was expressed in COS cells. The expressed Smad1 was immunoprecipitated from the cell lysate. After extensive washing, the immunoprecipitated Smad1 was mixed with $^{32}$P-labeled GST-fusion proteins of WWP1 WW domains. The binding products were washed and run on SDS-PAGE. COS extract and $^{32}$P-labeled GST protein was used as controls. WWP1.1 (a GST fusion with the 1st WW repeat: LPSGWEQRKDPHGR-TYYVDHNTRTTTWER PQPLPPGWE (SEQ ID NO:26) was found to bind to Smad1 (FIG. 4, lane 2), but not the Smad1 mutated at the PY motif (FIG. 4, lane 3). The Smad 1 PY peptide sequence used was: Biotin-Ahx-PADTPPPAY-LPPED-CONH$_2$ (SEQ ID NO:22), and the mutated Smad 1 PY peptide sequence was: Biotin-Ahx-PADTPPPAHL-PPED-CONH$_2$ (SEQ ID NO:27).

These results indicate that BMP induces ubiquitination of Smad proteins, using a pathway that includes a HECT E3 ubiquitin ligase.

Example 2

Interaction Between HECT E3 Ubiquitin Ligase WW Domain and Smad Proteins PY Motif Peptides This Example illustrates the binding of HECT E3 WW domains to PY motifs.

The HECT domain E3 ligase WWP1 has 4 WW domains (WWP1:1, 1.2, 1.3, 1.4) which interact with the WBP-1 PY motif peptide (Chen and Sudol, *Proc. Natl. Acad. Sci: USA* 92:7819-7823, 1995). The sequence for each domain is:
WWP1.1: LPSGWGWEQRKDPHGR-TYYVDHNTRTTTWERPQPLPPG (SEQ ID NO:10);
WWP1.2: QPLPPGWERRVD-DRRRVYYVDHNTRTTTWQRPTMESVR (SEQ ID NO:11);

WWP1.3: GPLPPGWEKRVDSTDRVYFVNHNTKT-TQWEDPRTQGLQ (SEQ ID NO:12;) and

WWP1.4: EPLPEGWEIRYTREGVRY-FVDHNTRTTTFKDPRNGKSS (SEQ ID NO:13)

Each domain was individually expressed as a GST fusion protein. A TRF binding assay was used to evaluate interactions of PY motif peptides with these domains or GST alone. WW domains were bound to a 96-well polystyrene assay plate (Costar) overnight at 4° C. in a 200 mM carbonate buffer (Pierce, Rockford, Ill.) at different concentrations (0, 1, 3, 10 µg/mL). Unbound WW domain was washed away with distilled, deionized water and the plates were blocked with 1% BSA/carbonate buffer for 2 hours at room temperature. The plates were then washed with Tris/TWEEN® buffer: 50 mM Tris pH 7.5, 100 mM NaCl, 1 mM EDTA, 1% BSA, 1 mM DTT, 0.1% TWEEN® 20 detergent, protease inhibitor cocktail (Boehringer-Mannheim).

PY motif peptides were synthesized with a $C_6$-linker and biotin tag. The following PY motifs were used:

WBP1: Biotin-Ahx-HPGTPPPPYTVGPG-CONH$_2$ (SEQ ID NO:28);

Nedd: Biotin-Ahx-IPGTPPPNYDSLRL-CONH$_2$ (SEQ ID NO:29);

Mutant Nedd: Biotin-Ahx-IPGTPPPNHDSLRL-CONH2 (SEQ ID NO:30).

These biotinylated peptides were solvated in Tris/TWEEN® buffer and added to the assay plates (30 µM). The plates were incubated at 4° C. for varying amounts of capture time. The plates were then washed with PBS/0.1% TRITON® X-100 detergent and probed for 1 hour at room temperature with 1 µg/mL Europium-labeled streptavidin (DELFIA; Wallac Oy, Turku, Finland) in DELFIA Assay Buffer/0.1% Triton X100. The unbound Europium-labeled streptavidin was washed with PBS/0.1% TRITON® X-100 detergent. Europium was released for time-resolved fluorescence measurements with the DELFIA Enhancement Buffer. Measurements were made on either the DELFIA 1234 or Victor fluorometers.

The WBP1 peptide bound specifically to the WWP1 WW domains but not to GST (FIGS. 5A-5D). The other biotinylated peptides did not specifically interact with the WW domains or GST (FIGS. 5A-5D).

Smad PY motif peptides from Smad 1, 2, 3, 5, 6 and 7 (Table 1) were then evaluated with the WW domains from WWP1 (FIGS. 6A-6D and 7A-7B). The GST-WW domain fusion proteins and GST alone were coated at 30 µg/mL overnight. After blocking the wells with BSA, the WW domain peptides were titrated with the Smad PY motif peptides. Smad 7 peptide demonstrated a very potent interaction with the second WW domain of WWP1 (WWP1.2; FIGS. 6A-6D); much more potent than the reported WBP1 PY peptide (FIGS. 5A-5D). The Smad 5 and Smad 6 peptides had measurable interactions with the WWP1 WW domains but were modest compared to the Smad 7 interactions (FIGS. 6A-6D and 7A-7B). There was no measurable interaction of PY motif peptides from Smad 1, 2 or 3.

TABLE I

| Smad Protein PY Motifs | |
|---|---|
| Smad Protein | PY Motif Peptide |
| Smad7 | ELESPPPPYSRYPM (SEQ ID NO:20) |
| Smad6 | GPESPPPPYSRLSP (SEQ ID NO:21) |
| Smad1 | PADTPPPAYLPPED (SEQ ID NO:22) |
| Smad5 | PADTPPPAYMPPDD (SEQ ID NO:23) |

TABLE I-continued

| Smad Protein PY Motifs | |
|---|---|
| Smad Protein | PY Motif Peptide |
| Smad2 | IPETPPPGYISEDG (SEQ ID NO:24) |
| Smad3 | AGLTPPPGYLSEDG (SEQ ID NO:25) |

Figure 8A:
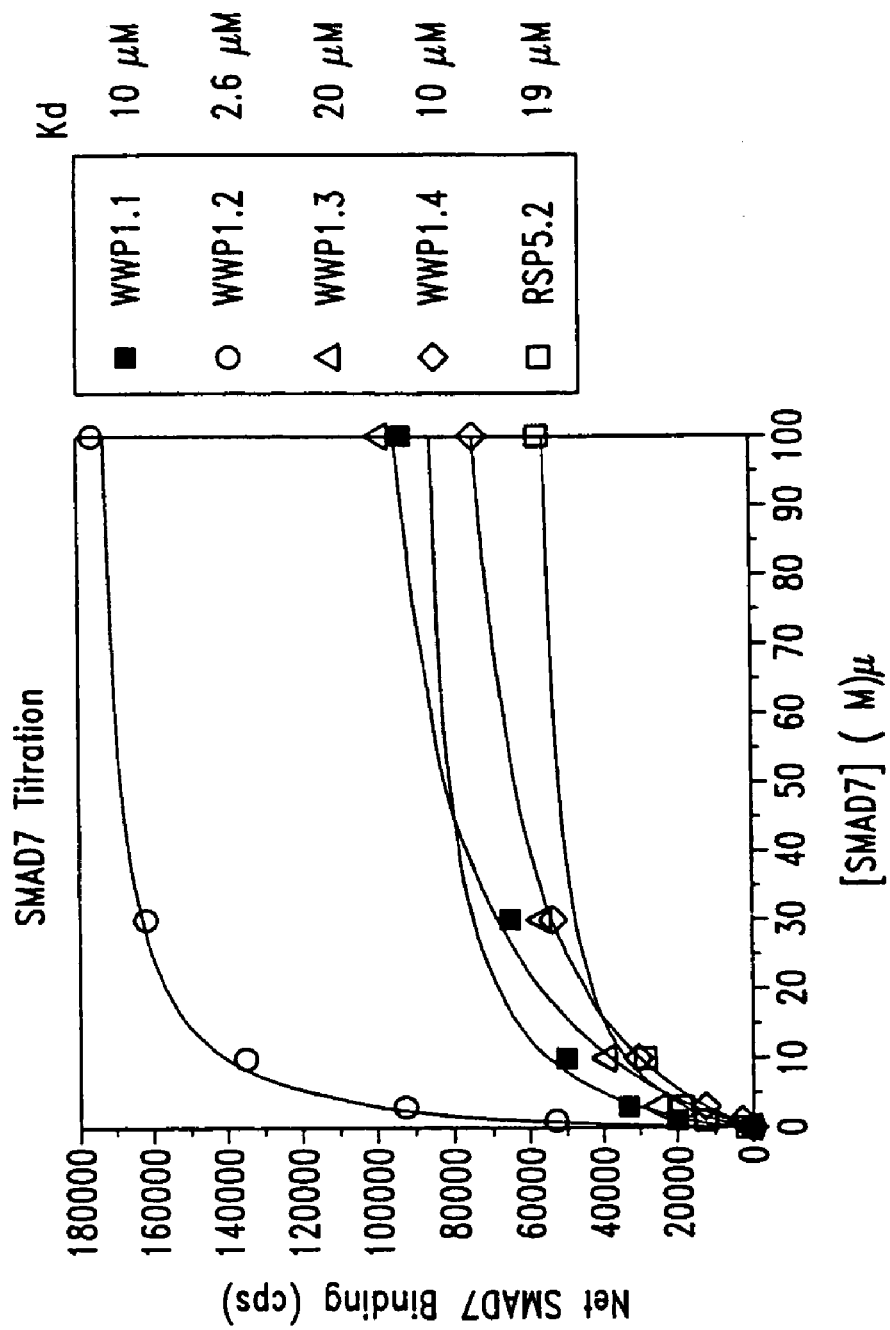
FIGS. 8A-8B are graphs illustrating the binding of increasing concentrations of a Smad7 PY motif peptide to WWP1 WW domain peptides.
Figure 8B:
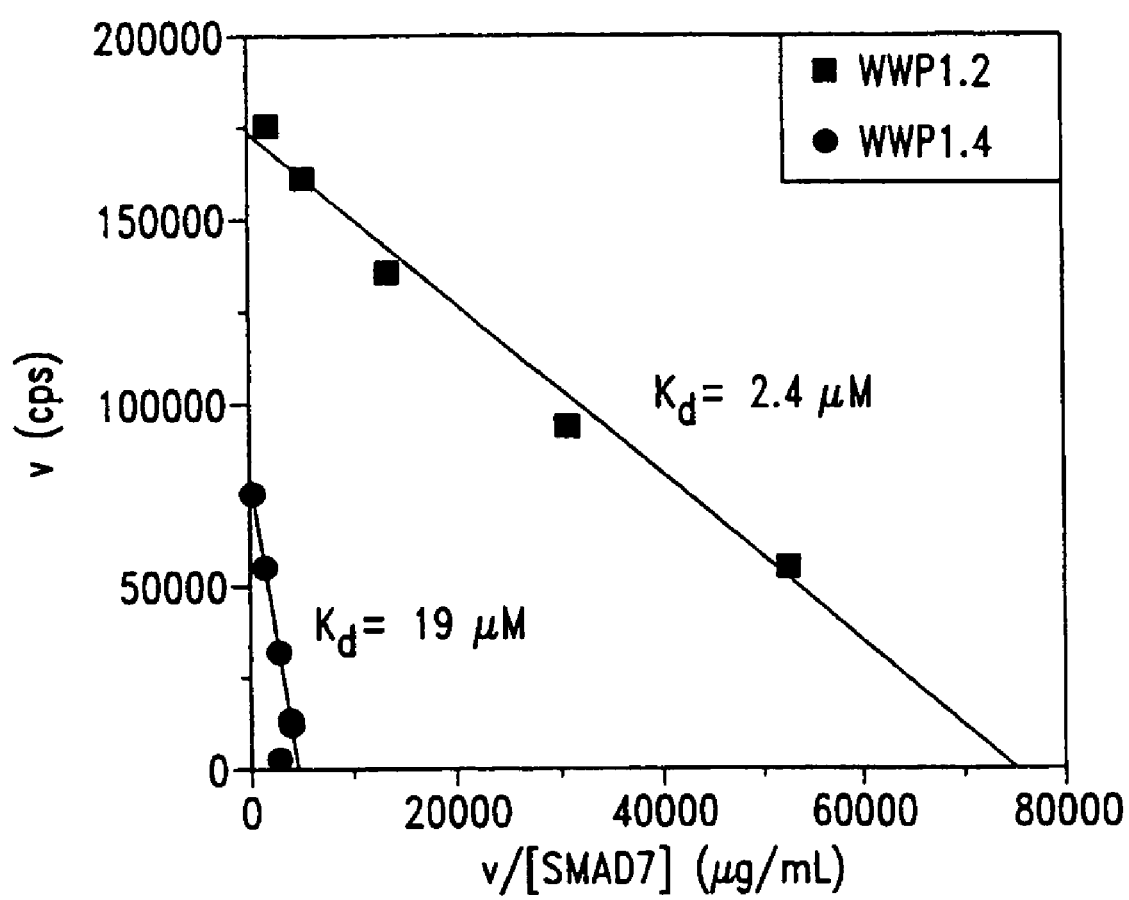

A detailed evaluation of the interaction of Smad 7 with the WWP: WW domains and the second WW domain from RSP5 was undertaken. GST was used to correct for non-specific background interactions. The peptide titration of the WW domains was evaluated by a nonlinear, least squares fit of the data and Scatchard analysis (FIGS. 8A-8B). Both methods showed that WWP1.2 had very specific interactions with Smad 7 peptide ($K_d$=2.4 82 M). Binding interactions from WWP1.1 and WWP1.3 did not yield a linear plot in the Scatchard analysis.

These results indicate the HECT E3 ubiquitin ligase WW domains bind to Smad protein PY motifs.

Example 3

Coupled Ubiquitin Assay for Detecting HECT E3 Ligase Ubiquitination

This Example illustrates a coupled enzymatic assay that evaluates the fate of a labeled ubiquitin molecule in the E1/E2/E3 pathway.

Recombinant E1 (ubc5c) and E2 (ubc7) components were obtained from BostonBiochem (Cambridge, Mass.). Radio-labeled ubiquitin was generated by PKA-mediated incorporation of [$^{32}$P]-phosphate from α-[$^{32}$P]-ATP to the PKA site of the GST-Ub fusion protein (pGEX KG expression vector). The ubiquitin assay buffer (UbB) was as follows: 50 mM Tris pH 7.6, 1 mM ATP, 0.2 mM EDTA, 5 mM MgCl$_2$, 1 unit inorganic pyrophosphatase, 0.005% TRITON® X-100 detergent and 1 µM staurosporine. In a 0.030 mL reaction, the following components were present: 50-200 ng E1, 0.1-1 µg E2 and 5 µg GST-Ub. Reactions were run at room temperature and terminated with a SDS-PAGE loading buffer that did not contain mercaptans. Reactions were analyzed by SDS-PAGE. The ubiquitination of active site cysteine residues of E1 and E2s (ubc 5c and ubc 7) was observed (FIGS. 9A-9C). The addition of 20 mM DTT prevented the formation of the thioester intermediates (FIGS. 9B-9C).

To evaluate transfer to a HECT E3 ligase, assays were performed as above, with the addition of 50-100 ng of the WWP1 HECT domain containing residues 611-985 or 611-990 of WWP1, as indicated. Sequences of these domains are shown below:

WWP1 HECT domain 611-985:

```
                                          (SEQ ID NO:31)
GFRWKLAHFRYLCQSNALPSHVKINVSRQTLFEDSFQQIMALKPYDLRR

RLYVIFRGEEGLDYGGLAREWFFLLSHEVLNPMYCLFEYAGKNNYCLQI

NPASTINPDHLSYFCFIGRFIAMALFHGKFIDTGFSLPFYKRMLSKKLTIK

DLESIDTEFYNSLIWIRDNNIEECGLEMYFSVDMEILGKVTSHDLKLGGS

NILVTEENKDEYIGLMTEWRFSRGVQEQTKAFLDGFNEVVPLQWLQYF

DEKELEVMLCGMQEVDLADWQRNTVYRHYTRNSKQIIWFWQFVKETD
```

-continued

NEVRMRLLQFVTGTCRLPLGGFAELMGSNGPRNSQKFCIEKVGKDTWL

PRSHTCFNRLDLPPYKSYEQLKEKLLFAIEETE

WWP1 HECT domain 611-990:

(SEQ ID NO:32)
GFRWKLAHFRYLCQSNALPSHVKINVSRQTLFEDSFQQIMALKPYDLRR

RLYVIFRGEEGLDYGGLAREWFFLLSHEVLNPMYCLFEYAGKNNYCLQI

NPASTINPDHLSYFCFIGRFIAMALFHGKFIDTGFSLPFYKRMLSKKLTIK

DLESIDTEFYNSLIWIRDNNIEECGLEMYFSVDMEILGKVTSHDLKLGGS

NILVTEENKDEYIGLMTEWRFSRGVQEQTKAFLDGFNEVVPLQWLQYF

DEKELEVMLCGMQEVDLADWQRNTVYRHYTRNSKQIIWFWQFVKETD

NEVRMRLLQFVTGTCRLPLGGFAELMGSNGPRNSQKFCIEKVGKDTWL

PRSHTCFNRLDLPPYKSYEQLKEKLLFAIEETEGFGQE

Figures 11A, 11B, 11C:
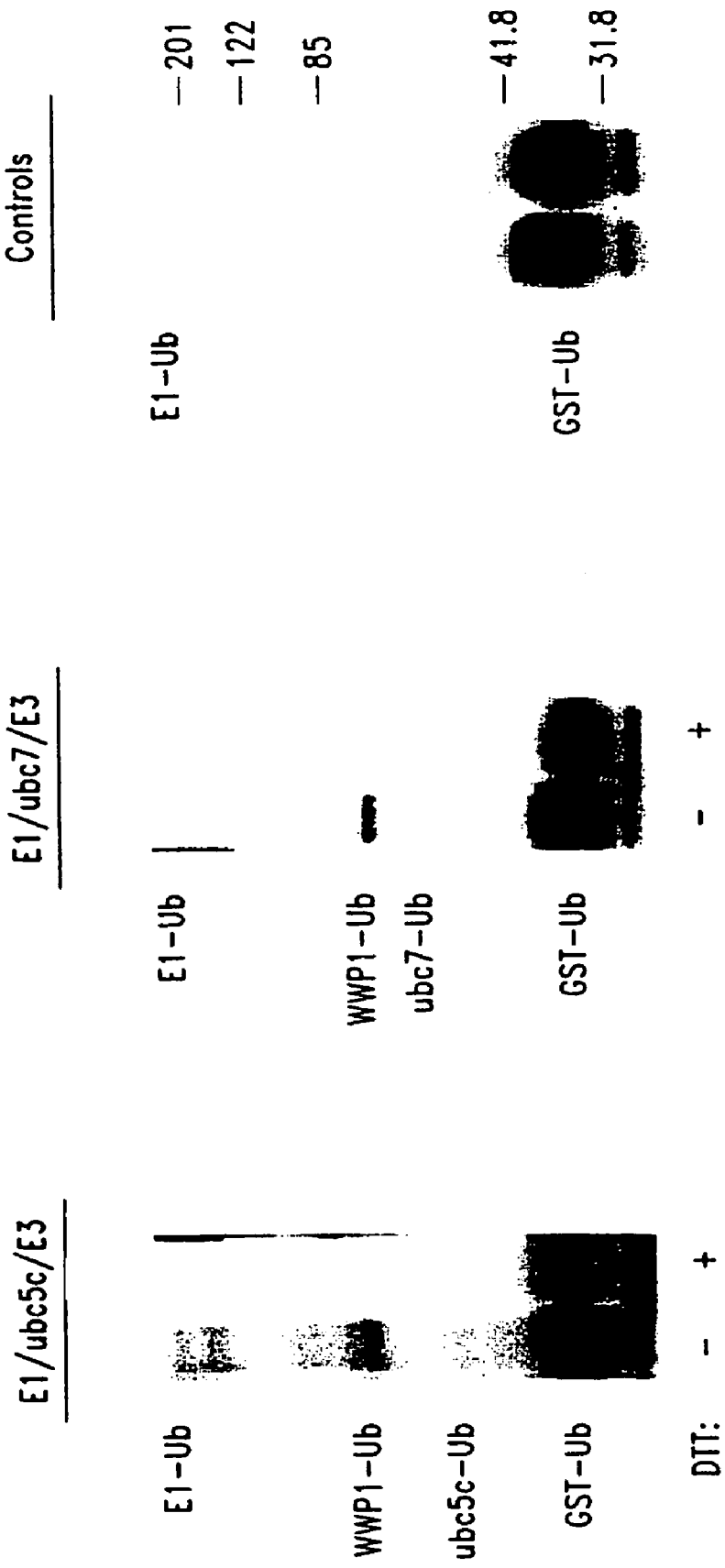
FIGS. 11A-11C are autoradiograms illustrating the ubiquitination of the HECT E3 ligase WWP1 in a coupled ubiquitination assay. In each Figure, incorporation of labeled ubiquitin into a WWP1 HECT domain containing residues 611-985 is shown. Also shown are ubiquitinated E1 and E2. Reactions were performed in the presence or absence of DTT, as indicated.

The HECT domain of WWP1 was shown to be charged by either E1/ubc5C or E1/ubc7 (FIGS. 10A-10C and 11A-11C). The shorter HECT domain, WWP1(611-985), only became charged with one ubiquitin molecule, presumably on its active site cysteine. The sensitivity of the ubiquitin adduct with WWP1(611-985) to DTT is consistent with the bond being to the active site cysteine (FIGS. 11A and 11B, compare lane 4 to lane 2). The longer HECT domain, WWP1(611-990), displayed a lack of substrate selectivity (FIGS. 10A and 10B). Time courses of the WWP1(611-990) reactions mediated by either ubc5c or ubc7 indicated that the E2 ubc5c was more efficient at activating WWP1(611-990) (FIGS. 12A-12C). The loss of GST-ubiquitin correlated with the appearance of high molecular species (>201 kDa).

These results confirm the role of HECT E3 ubiquitin ligases in Smad protein degradation.

From the foregoing, it will be appreciated that, although specific embodiments of the invention have been described herein for the purpose of illustration, various modification may be made without deviating from the spirit and scope of the invention. Accordingly, the present invention is not limited except by the appended claims.

The invention claimed is:

1. A method for screening for an agent that modulates BMP-mediated signaling, comprising:
   (a) contacting
      (i) a HECT E3 ubiquitin ligase WW domain, wherein the domain comprises SEQ ID NOS:1, 2, 3, 4, 5, 6, 7, 8, 9, 10, 11, 12, or 13;
      (ii) a Smad PY motif, wherein the motif comprises SEQ ID NOS: 14, 15, 16, 17, 20, 21, 22, 23, 24, or 25; and
      (iii) a candidate agent; under conditions that permit a detectable level of binding of the HECT E3 ubiquitin ligase WW domain to the Smad PY motif in the absence of the candidate agent; and
   (b) comparing the level of binding of the HECT E3 ubiquitin ligate WW domain to the Smad PY motif in the presence of the candidate agent to a control level of binding of the HECT E3 ubiquitin ligase WW domain to the Smad PY motif in the absence of candidate agent, and therefrom determining whether the candidate agent modulates BMP-mediated signaling.

2. The method according to claim 1, wherein the HECT E3 ubiquitin ligase WW domain comprises the sequence:
   Gly-Pro-Leu-Pro-Xaa-Gly-Trp-Glu-Xaa-Xaa-Xaa-Taa-Taa-Gly-Taa-Xaa-Tyr-Tyr-Haa-Xaa-His-Asn-Thr-Taa-Thr-Thr-Taa-Trp-Xaa-Taa-Pro-Taa (SEQ ID NO:2); wherein each Taa is an independently selected polar amino acid residue, Haa is a hydrophobic residue and each Xaa is an independently selected amino acid residue.

3. The method according to claim 1, wherein the Smad PY motif comprises the sequence Ser/Thr-Pro-Pro-Pro-Pro/Ala/Gly-Tyr (SEQ ID NO:15), wherein Ser/Thr is an amino acid residue that is serine or threonine and Pro/Ala/Gly is an amino acid residue that is selected from the group consisting of proline, alanine, and glycine.

4. The method according to claim 3, wherein the Smad PY motif comprises the sequence Thr-Pro-Pro-Pro-Ala-Tyr (SEQ ID NO:16), Thr-Pro-Pro-Pro-Gly-Tyr (SEQ ID NO:18) or Pro-Ala-Asp-Thr-Pro-Pro-Pro-Ala-Tyr-Leu/Met-Pro-Pro-Pro-Asp (SEQ ID NO:17), wherein Leu/Met is an amino acid residue that is leucine or threonine.

5. The method according to claim 1, wherein the candidate agent is a small molecule within a combinatorial library.

6. The method according to claim 1, wherein the HECT E3 ubiquitin ligase WW domain is immobilized on a solid support and the Smad PY motif comprises a tag.

7. The method according to claim 1, wherein the Smad PY motif is immobilized on a solid support and the HECT E3 ubiquitin ligase WW domain comprises a tag.

8. The method according to claim 6 or claim 7, wherein the tag is biotin or a radioactive group.

9. The method according to claim 1, wherein the level of binding is determined via a two-antibody sandwich assay.

10. The method according to claim 1, wherein the level of binding is determined via a competitive assay.

11. The method according to claim 2, wherein each Taa is selected from the amino acid residue group consisting of Ser, His, Pro, Asp, Glu, Thr, and Tyr.

12. The method according to claim 2, wherein each Haa is selected from the hydrophobic residue group consisting of Ile, Val, Leu, and Met.

13. The method of claim 1, wherein:
   (i) when the level of binding of the HECT E3 ubiquitin ligase WW domain to the Smad PY motif is increased as compared to the control level, the agent decreases BMP-mediated signaling, or
   (ii) when the level of binding of the HECT E3 ubiquitin ligase WW domain to the Smad PY motif is decreased as compared to the control level, the agent increases BMP-mediated signaling.

14. The method of claim 1, wherein said determining whether the candidate agent modulates BMP-mediated signaling further comprises the step of measuring or otherwise determining the level of Smad ubiquitination in the presence of the agent as compared to in the absence of the agent, wherein:
   (i) an increase in Smad ubiquitination indicates the agent decreases BMP-mediated signaling, or
   (ii) a decrease in Smad ubiquitination indicates the agent increases BMP-mediated signaling.

15. The method of claim 1, wherein said determining whether the candidate agent modulates BMP-mediated signaling further comprises the step of measuring or otherwise determining the level of Smad protein in the presence of the agent as compared to in the absence of the agent, wherein:

(i) an increase in Smad protein indicates the agent increases BMP-mediated signaling, and (ii) a decrease in Smad protein indicates the agent decreases BMP-mediated signaling.

16. The method of claim 1, wherein said HECT E3 ubiquitin ligase WW domain consists of the amino acid sequence of SEQ ID NOS:1, 2, 3, 4, 5, 6 7, 8, 9, 10, 11, 12, or 13.

17. The method of claim 1, wherein said Smad PY motif consists of SEQ ID NOS:14, 15, 16, 17, 20, 21, 22, 23, 24, or 25.

18. The method of claim 1, wherein said HECT E3 ubiquitin ligase WW domain consists of the amino acid sequence of SEQ ID NO:1, 2, 3, 4, 5, 6, 7, 8, 9, 10, 11, 12, or 13; and wherein said Smad PY motif consists of SEQ ID NOS:14, 15, 16, 17, 20, 21, 22, 23, 24, or 25.

* * * * *